(12) United States Patent
Willis

(10) Patent No.: US 7,931,590 B2
(45) Date of Patent: Apr. 26, 2011

(54) TISSUE STABILIZER AND METHODS OF USING THE SAME

(75) Inventor: Geoffrey Willis, Redwood City, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 479 days.

(21) Appl. No.: 10/283,784

(22) Filed: Oct. 29, 2002

(65) Prior Publication Data

US 2004/0082837 A1    Apr. 29, 2004

(51) Int. Cl.
*A61B 1/32* (2006.01)

(52) U.S. Cl. .......................................... 600/219

(58) Field of Classification Search ................ 600/184, 600/201, 210, 215, 216, 219, 235
See application file for complete search history.

(56) References Cited

U.S. PATENT DOCUMENTS

| | | | |
|---|---|---|---|
| 452,131 A | 5/1891 | Haughawout |
| 1,706,500 A | 3/1929 | Smith |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,392,722 A | 7/1968 | Jorgensen |
| 3,466,079 A | 9/1969 | Mammel |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jacobs |
| 3,858,926 A | 1/1975 | Ottenhues |
| 3,882,855 A | 5/1975 | Schulte et al. |
| 3,912,317 A | 10/1975 | Ohnaka et al. |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |

(Continued)

FOREIGN PATENT DOCUMENTS

AU    713601    3/2000

(Continued)

OTHER PUBLICATIONS

U.S. Appl. No. 09/345,859, Looney et al. filed Jul. 1, 1999.

(Continued)

*Primary Examiner* — Anu Ramana
(74) *Attorney, Agent, or Firm* — Law Office of Alan W. Cannon

(57) ABSTRACT

Devices and methods are provided for stabilizing tissue, e.g., a beating heart, within a patient's body. In certain embodiments, the subject devices are characterized by having a shaft and at least two contacting members operatively associated with the shaft where the contacting members are capable of assuming a substantial coaxial alignment when in a low profile configuration and also capable of assuming an open, working configuration. In other embodiments, the devices are characterized by having a shaft and at least one tissue contacting member associated with the shaft using a ball and socket mechanism, wherein the at least one tissue contacting member may be caused to pitch and/or roll and/or yaw. In the subject methods, a subject device is advanced to the target site and stabilizes the target tissue using compression, negative pressure or both. The subject invention also includes kits for use in practicing the subject methods.

36 Claims, 8 Drawing Sheets

U.S. PATENT DOCUMENTS

| | | | |
|---|---|---|---|
| 4,049,484 A | 9/1977 | Priest et al. | |
| 4,052,980 A | 10/1977 | Grams et al. | |
| 4,094,484 A | 6/1978 | Galione | |
| 4,096,853 A | 6/1978 | Weigand | |
| 4,217,890 A | 8/1980 | Owens | |
| 4,226,228 A | 10/1980 | Shin et al. | |
| 4,230,119 A | 10/1980 | Blum | |
| 4,306,561 A | 12/1981 | de Medinaceli | |
| 4,350,160 A | 9/1982 | Kolesov et al. | |
| 4,366,819 A | 1/1983 | Kaster | |
| 4,368,736 A | 1/1983 | Kaster | |
| 4,421,107 A | 12/1983 | Estes et al. | |
| 4,428,368 A | 1/1984 | Torii | |
| 4,434,791 A | 3/1984 | Darnell | |
| 4,457,300 A | 7/1984 | Budde | |
| 4,461,284 A | 7/1984 | Fackler | |
| 4,492,229 A | 1/1985 | Grunwald | |
| 4,617,916 A | 10/1986 | LeVahn et al. | |
| 4,627,421 A | 12/1986 | Symbas et al. | |
| 4,637,377 A | 1/1987 | Loop | |
| 4,646,747 A | 3/1987 | Lundback | |
| 4,688,570 A | 8/1987 | Kramer et al. | |
| 4,702,230 A | 10/1987 | Pelta | |
| D293,470 S | 12/1987 | Adler | |
| 4,718,418 A | 1/1988 | L-Esperance, Jr. | |
| 4,726,356 A | 2/1988 | Santilli et al. | |
| 4,726,358 A | 2/1988 | Brady | |
| 4,736,749 A | 4/1988 | Lundback | |
| 4,747,395 A | 5/1988 | Brief | |
| 4,754,746 A | 7/1988 | Cox | |
| 4,803,984 A | 2/1989 | Narayanan et al. | |
| 4,808,163 A | 2/1989 | Laub | |
| 4,827,926 A | 5/1989 | Carol | |
| 4,829,985 A | 5/1989 | Couetil | |
| 4,852,552 A | 8/1989 | Chaux | |
| 4,854,318 A | 8/1989 | Solem et al. | |
| 4,858,552 A | 8/1989 | Glatt et al. | |
| 4,863,133 A | 9/1989 | Bonnell | |
| 4,865,019 A | 9/1989 | Phillips | |
| 4,884,559 A | 12/1989 | Collins | |
| 4,904,012 A | 2/1990 | Nishiguchi et al. | |
| 4,925,443 A | 5/1990 | Heilman et al. | |
| 4,949,707 A | 8/1990 | LeVahn et al. | |
| 4,949,927 A | 8/1990 | Madocks et al. | |
| 4,955,896 A | 9/1990 | Freeman | |
| 4,957,477 A | 9/1990 | Lundbach | |
| 4,962,758 A | 10/1990 | Lasner et al. | |
| 4,971,037 A | 11/1990 | Pelta | |
| 4,973,300 A | 11/1990 | Wright | |
| 4,989,587 A | 2/1991 | Farley | |
| 4,991,578 A | 2/1991 | Cohen | |
| 4,993,862 A | 2/1991 | Pelta | |
| 5,009,660 A | 4/1991 | Clapham | |
| 5,011,469 A | 4/1991 | Buckberg et al. | |
| 5,019,086 A | 5/1991 | Neward | |
| 5,025,779 A | 6/1991 | Bugge | |
| 5,036,868 A | 8/1991 | Berggren et al. | |
| 5,037,428 A | 8/1991 | Picha et al. | |
| 5,052,373 A | 10/1991 | Michelson | |
| 5,053,041 A | 10/1991 | Ansari et al. | |
| 5,080,088 A | 1/1992 | LeVahn | |
| 5,098,369 A | 3/1992 | Heilman et al. | |
| 5,119,804 A | 6/1992 | Anstadt | |
| 5,125,395 A | 6/1992 | Adair | |
| 5,131,905 A | 7/1992 | Grooters et al. | |
| 5,133,724 A | 7/1992 | Wilson, Jr. et al. | |
| 5,139,517 A | 8/1992 | Corral | |
| 5,150,706 A | 9/1992 | Cox et al. | |
| 5,152,777 A | 10/1992 | Goldberg et al. | |
| 5,159,921 A | 11/1992 | Hoover | |
| RE34,150 E | 12/1992 | Santilli et al. | |
| 5,167,223 A | 12/1992 | Koros et al. | |
| 5,171,254 A | 12/1992 | Sher | |
| 5,192,070 A | 3/1993 | Nagai et al. | |
| 5,196,003 A | 3/1993 | Bilweis | |
| 5,231,974 A | 8/1993 | Giglio et al. | |
| 5,256,132 A | 10/1993 | Snyders | |
| 5,287,861 A | 2/1994 | Wilk | |
| 5,290,082 A | 3/1994 | Palmer et al. | |
| 5,293,863 A | 3/1994 | Zhu et al. | |
| 5,300,087 A * | 4/1994 | Knoepfler | 606/207 |
| 5,318,013 A | 6/1994 | Wilk | |
| 5,336,252 A | 8/1994 | Cohen | |
| 5,348,259 A | 9/1994 | Blance et al. | |
| 5,363,882 A | 11/1994 | Chikama | |
| 5,382,756 A | 1/1995 | Dagan | |
| 5,383,840 A | 1/1995 | Heilman et al. | |
| 5,417,709 A | 5/1995 | Slater | |
| 5,425,705 A * | 6/1995 | Evard et al. | 604/28 |
| 5,437,651 A | 8/1995 | Todd et al. | |
| 5,452,733 A | 9/1995 | Sterman et al. | |
| 5,453,078 A | 9/1995 | Valentine et al. | |
| 5,467,763 A | 11/1995 | McMahon et al. | |
| 5,480,425 A | 1/1996 | Ogilive | |
| 5,484,391 A | 1/1996 | Buckman, Jr. et al. | |
| 5,498,256 A | 3/1996 | Furnish | |
| 5,503,617 A | 4/1996 | Jako | |
| 5,509,890 A | 4/1996 | Kazama | |
| 5,512,037 A | 4/1996 | Russell et al. | |
| 5,514,075 A | 5/1996 | Moll et al. | |
| 5,514,076 A | 5/1996 | Ley | |
| 5,520,610 A | 5/1996 | Giglio et al. | |
| 5,522,819 A | 6/1996 | Graves et al. | |
| 5,529,571 A | 6/1996 | Daniel | |
| 5,536,251 A | 7/1996 | Evard et al. | |
| 5,547,458 A | 8/1996 | Ortiz et al. | |
| 5,569,274 A | 10/1996 | Rapacki et al. | |
| 5,571,074 A | 11/1996 | Buckman, Jr. et al. | |
| 5,571,215 A | 11/1996 | Sterman et al. | |
| 5,573,496 A | 11/1996 | McPherson et al. | |
| 5,582,580 A | 12/1996 | Buckman, Jr. et al. | |
| 5,607,421 A | 3/1997 | Jeevanandam et al. | |
| 5,607,446 A | 3/1997 | Beehler et al. | |
| 5,613,937 A | 3/1997 | Garrison et al. | |
| 5,632,746 A | 5/1997 | Middleman et al. | |
| 5,651,378 A | 7/1997 | Matheny et al. | |
| 5,662,300 A | 9/1997 | Michelson | |
| 5,667,480 A | 9/1997 | Knight et al. | |
| 5,713,951 A | 2/1998 | Garrison et al. | |
| 5,727,569 A | 3/1998 | Benetti et al. | |
| 5,728,151 A | 3/1998 | Garrison et al. | |
| 5,730,757 A | 3/1998 | Benetti et al. | |
| 5,735,290 A | 4/1998 | Sterman et al. | |
| 5,749,892 A * | 5/1998 | Vierra et al. | 600/204 |
| 5,755,660 A | 5/1998 | Tyagi | |
| 5,766,151 A | 6/1998 | Valley et al. | |
| 5,772,583 A | 6/1998 | Wright et al. | |
| 5,782,746 A | 7/1998 | Wright | |
| 5,795,291 A | 8/1998 | Koros et al. | |
| 5,797,960 A | 8/1998 | Stevens et al. | |
| 5,799,661 A | 9/1998 | Boyd et al. | |
| 5,807,243 A * | 9/1998 | Vierra et al. | 600/204 |
| 5,813,410 A | 9/1998 | Levin | |
| 5,836,311 A | 11/1998 | Borst et al. | |
| 5,846,187 A | 12/1998 | Wells et al. | |
| 5,846,193 A | 12/1998 | Wright | |
| 5,846,194 A | 12/1998 | Wasson et al. | |
| 5,865,730 A | 2/1999 | Fox et al. | |
| 5,868,770 A | 2/1999 | Rygaard | |
| 5,875,782 A | 3/1999 | Ferrari et al. | |
| 5,876,332 A | 3/1999 | Looney | |
| 5,879,291 A | 3/1999 | Kolata et al. | |
| 5,882,299 A | 3/1999 | Rastegar et al. | |
| 5,885,271 A | 3/1999 | Hamilton et al. | |
| 5,888,247 A | 3/1999 | Benetti | |
| 5,891,017 A | 4/1999 | Swindle et al. | |
| 5,894,843 A | 4/1999 | Benetti et al. | |
| 5,899,425 A | 5/1999 | Corey et al. | |
| 5,906,607 A | 5/1999 | Taylor et al. | |
| 5,908,382 A | 6/1999 | Koros et al. | |
| 5,913,876 A | 6/1999 | Taylor et al. | |
| 5,927,284 A | 7/1999 | Borst et al. | |
| 5,944,658 A | 8/1999 | Koros et al. | |
| 5,944,736 A | 8/1999 | Taylor et al. | |
| 5,947,125 A | 9/1999 | Benetti | |
| 5,947,896 A | 9/1999 | Sherts et al. | |
| 5,957,835 A | 9/1999 | Anderson et al. | |

| | | | |
|---|---|---|---|
| 5,961,481 A | 10/1999 | Sterman et al. | |
| 5,967,972 A | 10/1999 | Santilli et al. | |
| 5,967,973 A | 10/1999 | Sherts et al. | |
| 5,976,080 A | 11/1999 | Farascioni | |
| 5,976,171 A | 11/1999 | Taylor | |
| 5,984,864 A | 11/1999 | Fox et al. | |
| 5,984,865 A | 11/1999 | Farley et al. | |
| 5,984,867 A | 11/1999 | Deckman et al. | |
| 6,007,486 A | 12/1999 | Hunt et al. | |
| 6,007,523 A | 12/1999 | Mangosong | |
| 6,010,531 A | 1/2000 | Donlon et al. | |
| 6,013,027 A | 1/2000 | Khan et al. | |
| 6,015,378 A | 1/2000 | Borst et al. | |
| 6,017,304 A | 1/2000 | Vierra et al. | |
| 6,019,722 A | 2/2000 | Spence et al. | |
| 6,027,476 A | 2/2000 | Sterman et al. | |
| 6,029,671 A | 2/2000 | Stevens et al. | |
| 6,030,340 A | 2/2000 | Maffei et al. | |
| D421,803 S | 3/2000 | Koros et al. | |
| 6,032,672 A | 3/2000 | Taylor | |
| 6,033,362 A | 3/2000 | Cohn | |
| 6,036,641 A | 3/2000 | Taylor et al. | |
| 6,042,539 A | 3/2000 | Harper et al. | |
| 6,050,266 A | 4/2000 | Benetti et al. | |
| 6,063,021 A | 5/2000 | Hossain et al. | |
| 6,071,295 A | 6/2000 | Takahashi | |
| 6,099,468 A | 8/2000 | Santilli et al. | |
| 6,102,853 A | 8/2000 | Scirica et al. | |
| 6,102,854 A | 8/2000 | Carfier et al. | |
| 6,110,187 A | 8/2000 | Donlon | |
| 6,139,492 A | 10/2000 | Vierra et al. | |
| 6,149,583 A | 11/2000 | Vierra et al. | |
| 6,152,874 A | 11/2000 | Looney et al. | |
| 6,167,889 B1 | 1/2001 | Benetti | |
| 6,183,486 B1 | 2/2001 | Snow et al. | |
| 6,190,311 B1 | 2/2001 | Glines et al. | |
| 6,193,652 B1 | 2/2001 | Berky et al. | |
| 6,193,732 B1 | 2/2001 | Frantzen et al. | |
| 6,200,263 B1 | 3/2001 | Person | |
| 6,210,323 B1 | 4/2001 | Gilhuly et al. | |
| 6,213,940 B1 | 4/2001 | Sherts et al. | |
| 6,213,941 B1 | 4/2001 | Benetti et al. | |
| 6,231,506 B1 | 5/2001 | Hu et al. | |
| 6,231,585 B1 | 5/2001 | Takahashi et al. | |
| 6,251,065 B1 | 6/2001 | Kochamba | |
| 6,264,605 B1 | 7/2001 | Scirica et al. | |
| 6,283,912 B1 | 9/2001 | Hu et al. | |
| 6,290,644 B1 | 9/2001 | Green, II et al. | |
| 6,315,717 B1 | 11/2001 | Benetti et al. | |
| 6,331,158 B1 | 12/2001 | Hu et al. | |
| 6,334,843 B1 | 1/2002 | Borst et al. | |
| 6,336,898 B1 | 1/2002 | Borst et al. | |
| 6,346,077 B1 | 2/2002 | Taylor et al. | |
| 6,348,036 B1 | 2/2002 | Looney et al. | |
| 6,350,229 B1 | 2/2002 | Borst et al. | |
| 6,364,826 B1 | 4/2002 | Borst et al. | |
| 6,371,906 B1 | 4/2002 | Borst et al. | |
| 6,371,910 B1 | 4/2002 | Zwart et al. | |
| 6,375,611 B1 | 4/2002 | Voss et al. | |
| 6,383,134 B1 * | 5/2002 | Santilli | 600/205 |
| 6,394,948 B1 | 5/2002 | Borst et al. | |
| 6,394,951 B1 | 5/2002 | Taylor et al. | |
| 6,398,726 B1 | 6/2002 | Ramans et al. | |
| 6,406,424 B1 | 6/2002 | Williamson, IV et al. | |
| 6,447,443 B1 * | 9/2002 | Keogh et al. | 600/37 |
| 6,458,079 B1 | 10/2002 | Cohn et al. | |
| 6,464,629 B1 | 10/2002 | Boone et al. | |
| 6,464,630 B1 | 10/2002 | Borst et al. | |
| 6,468,265 B1 | 10/2002 | Evans et al. | |
| 6,475,142 B1 | 11/2002 | Parsons et al. | |
| 6,478,029 B1 | 11/2002 | Boyd et al. | |
| 6,478,729 B1 | 11/2002 | Rogers et al. | |
| 6,482,151 B1 | 11/2002 | Vierra et al. | |
| 6,494,211 B1 | 12/2002 | Boyd et al. | |
| 6,503,245 B2 | 1/2003 | Palmer et al. | |
| 6,506,149 B2 | 1/2003 | Peng et al. | |
| 6,511,416 B1 * | 1/2003 | Green et al. | 600/37 |
| 6,537,212 B2 | 3/2003 | Sherts et al. | |
| 6,565,508 B2 | 5/2003 | Scirica et al. | |
| 6,589,166 B2 | 7/2003 | Knight et al. | |
| 6,592,573 B2 | 7/2003 | Castaneda et al. | |
| 6,602,183 B1 * | 8/2003 | Levi et al. | 600/37 |
| 6,607,479 B1 | 8/2003 | Kochamba et al. | |
| 6,610,008 B1 | 8/2003 | Spence et al. | |
| 6,610,009 B2 | 8/2003 | Person et al. | |
| 6,613,039 B1 * | 9/2003 | Namba | 604/541 |
| 6,701,930 B2 | 3/2004 | Benetti et al. | |
| 6,800,058 B2 * | 10/2004 | Jahns et al. | 600/210 |
| 810,675 A1 | 1/2006 | Richter | |
| 2003/0158463 A1 * | 8/2003 | Julian et al. | 600/104 |

FOREIGN PATENT DOCUMENTS

| | | |
|---|---|---|
| CA | 2197608 | 2/2000 |
| DE | 31 38 589 A1 | 4/1983 |
| DE | 90 04513 | 6/1990 |
| DE | 41 39 695 A1 | 6/1993 |
| EP | 0 293 760 A2 | 12/1988 |
| EP | 0 293 760 A3 | 12/1988 |
| EP | 0 293 760 B1 | 12/1988 |
| EP | 0 630 629 | 5/1994 |
| EP | 668 058 A1 | 8/1995 |
| EP | 0791 330 A2 | 8/1997 |
| EP | 0 803 228 A1 | 10/1997 |
| EP | 0 808 606 A1 | 11/1997 |
| EP | 0 919 193 A1 | 6/1999 |
| EP | 0 993 806 A2 | 4/2000 |
| FR | 473451 | 1/1915 |
| GB | 168216 | 9/1921 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A2 | 9/1997 |
| WO | WO 97/32514 A3 | 9/1997 |
| WO | WO 97/40752 | 11/1997 |
| WO | WO 98/27869 | 7/1998 |
| WO | WO 98/48703 | 11/1998 |
| WO | WO 98/49944 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 99/60929 A2 | 12/1999 |
| WO | WO 99/60930 A3 | 12/1999 |
| WO | WO 00/06041 | 2/2000 |
| WO | WO 00/10466 | 3/2000 |
| WO | WO 00/16367 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

U.S. Appl. No. 09/438,670 Parsons, et al. filed Nov. 12, 1999.
U.S. Appl. No. 09/489,274 Brown et al. filed Jan. 21, 2000.
U.S. Appl. No. 60/117,333, Looney et al. filed Jan. 24, 1999.
Akins, et al., "*Preservation of Interventricular Septal Function in Patients Having Coronary Artery Bypass Graft Without Cardiopulmonary Bypass,*" American Heart Journal, vol. 107, No. 2, Feb. 1984, pp. 304-309.
Ancalmo, N. and J. L. Ochsner: "*A Modified Sternal Retractor,*" Ann. Thorac, Surg. 21 (1976) 174.
Angelini, G.D., M.D. et al., "*Fiber-Optic Retractor for Harvesting the Internal Mammary Artery,*" Ann. Thorac. Surg. (1990; 50:314-5).
Angelini, G.D., M.D., "*A Simple, Inexpensive Method of Heart Retraction During Coronary Artery Bypass Surgery,*" Ann. Thora. Surg 46:46-247, Aug. 1988.

Anstadt, M.D., et al., "*Direct Mechanical Ventricular Actuation for Cardiac Arrest in Humans*," Chest, vol. 100, No. 1, Jul. 1991.

Antinori, C. et al., "*A Method of Retraction During Reoperative Coronary Operations Using the Favaloro Retractor*," The Society of Thoracic Surgeons: 1989.

Archer, DO, et al., "*Coronary Artery Revascularization Without Cardiopulmonary Bypass*," Texas Heart Institute Journal, vol. 11, No. 1, Mar. 1984, pp. 52-57.

Arom, K.V., et al., "Mini-Sternotomy for Coronary Artery Bypass Grafting," The Annals of Thoracic Surgery 1996; 61:1271-2.

Arom, K.V., et al., "Mini-Sternotomy for Coronary Artery Bypass Grafting," The Annals of Thoracic Surgery 1996; 62:1884-85.

Ballantyne, M.D., et al., "*Delayed Recovery of Severally—Stunned-Myocardium with the Support of a Left Ventricular Assist Device After Coronary Artery Bypass Graft Surgery*," Journal of the American College of Cardiology, vol. 10, No. 3, Sep. 1987, pp. 710-712.

Bedellino, M.M., et al., "*The Cardiac Rag—Simple Exposure of the Heart*," Texas Heart Institute Journal, vol. 15, No. 2, 1988, 134-35.

Beg, R.A., et al., "*Internal Mammary Retractor*," Ann Thorac, Surg., vol. 39, No. 1, pp. 286-287, Jan. 1985.

Benetti, et al., "*Direct Coronary Surgery with Saphenous Vein Bypass Without Either Cardiopulmonary Bypass or Cardiac Arrest*," The Journal of Cardiovascular Surgery, vol. 26, No. 3, May-Jun. 1985, pp. 217-222.

Benetti, et al., "*Direct Myocardial Revascularization Without Extracorporeal Circulation*," Chest, vol. 100, No. 2 Aug., 1991, pp. 312-316.

Benetti, F.J., "*Coronary Revascularization with Arterial Conduits Via a Small Thoracotomy and Assisted by Thoracoscopy, Atlhough Without Cardiopulmonary Bypass*," Cor Europaeum 4 (1) 2224 (1995).

Benetti, J., et al., "*A Single Coronary Artery Bypass Grafting—A Comparison Between Minimally Invasive Off Pump Techniques and Conventional Procedures*," European Journal of Cardio-Thoracic Surgery, 14 (Supp. I) (1998) S7-S12.

Borst, et al., "*Coronary Artery Bypass Grafting Without Cardiopulmonary Bypass and Without Interruption of Native Coronary Flow Using a Novel Anastomosis Site Restraining Device ('Octopus')*," J Am Coll Cardiol, May 1996, vol. 27, No. 6, pp. 1356-1364.

Borst, et al., "*Regional Cardiac Wall Immunobilization for Open Chest and Closed Chest Coronary Artery Bypass Grafting on the Beating Heart; -Octopus- Method*," Circulation, Oct. 15, 1995, vol. 92, No. 8, supplement 1, 1-177.

British Heart Journal, "Coronary Surgery Without Cardiopulmonary Bypass," pp. 203-205, 1995.

Buffolo, et al., "*Direct Myocardial Revascularization Without Cardiopulmonary Bypass*," Thoac. Cardiovasc. Surgeon, 33 (1985) pp. 26-29.

Bugge, M., "*A New Internal Mammary Artery Retractor*," Thorac. Cardiovasc Surgeon 38, pp. 316-317 (1990).

Calafiore, A. M., et al., "*Minimally Invasive Coronary Artery Bypass Grafting*," The Annals of Thoracic Surgery, 62:1545-8, 1996.

Calvin (1990) "Circumflex Exposure Using a Cardiac Sling." Ann Thorac Surg., vol. 49:833-4.

Campalani et al., "A New Self-Retaining Internal mammary Artery Retractor." *J Cardiovas. Surg.*, vol. 28. (1987).

Cartier, R, MD., "*Triple Coronary Artery Revascularization on the Stabilized Beating Heart: Initial Experience*," Montreal Heart Institute, CJS, vol. 41, No. 4, pp. 283-288, Aug. 1998.

Chaux, A. and C. Blanche, "*A New Concept in Sternal Retraction: Applications for Internal Mammary Artery Dissection and Valve Replacement Surgery*," Ann. Thorac. Surg. 42, pp. 473-474, Oct. 1986.

Cooley, D. A., "*Limited Access Myocardial Revascularization*," Texas Heart Institute Journal, pp. 81-84, vol. 23, No. 2, 1996.

*Correspondence and Brief Communications*, Archives of Surgery—vol. 115, 1136-37, Sep. 1980.

Cremer, J, MD, "*Off-Bypass Coronary Bypass Grafting Via Minithoracotomy Using Mechanical Epicardial Stabilization*," The Annals of Thoracic Surgery, 63:S79-83, 1997.

Delacroix-Chevalier Surgical Instruments, IMA Saving Packages Brochure.

DelRossi, A J and Lemole, GM, "*A New Retractor to Aid in Coronary Artery Surgery*," The Annals of Thoracic Surgery, vol. 36, No. 1, 101-102, Jul. 1983.

Fanning, MD., "*Reoperative Coronary Artery Bypass Grafting Without Cardiopulmonary Bypass*," The Annals of Thoracic Surgery, vol. 55, No. 2, Feb. 1993, pp. 486-489.

Favaloro, M.D., et al, "*Direct Myocardial Revascularization by Saphenous Vein Graft*," The Annals of Thoracic Surgery, vol. 10, No. 2, Aug. 1970.

Fonger, et al., "*Enhanced Preservation of Acutely Ischemic Myocardium with Transeptal Left Ventricular Assist*," The Annals of Thoracic Surgery, vol. 57, No. 3, Mar. 1994, pp. 570-575.

Gacioch, et al., "*Cardiogenic Shock Complicating Acute Myocardial Infarction: The Use of Coronary Angioplasty and the Integracion of the New Support Device into Patient Management*," Journal of the American College of Cardiology, vol. 19, No. 3, Mar. 1, 1992.

Green, GE., "*Technique of Internal Mammary-Coronary Artery Anastomosis*," The Journal of Cardiovascular Surgery, 78:455-79, 1979.

Groopman, J., "*Heart Surgery, Unplugged; Making the Coronary Bypass Safer, Cheaper, and Easier*," The New Yorker, Jan. 11, 1999, pp. 43-46, 50-51.

Guzman, F. M.D., "*Transient Radial Nerve Injury Related to the Use of A Self Retraining Retractor for Internal Mammary Artery Dissection*," J. Cardiovasc. Surg. 30, 1989, pp. 1015-1016.

Hasan, RI, et al., "*Technique of Dissecting the Internal Mammary After Using the Moussalli Bar*," European Journal of Cardiothoracic Surgery, 4:571-572, 1990.

Itoh, Toshiaki, M.D., et al., "*New Modification of a Mammary Artery Retractor*," Ann. Thorac. Surg. 9, 1994; 57:1670-1.

Izzat, FRCS, et al., "*Cardiac Stabilizer for Minimally Invasive Direct Coronary Artery Bypass*," Elsevier Science Inc., 1997 by the Society of Thoracic Surgeons.

Janke "Heart Support for Coronary Bypass Surgery Involving the Circumflex Artery System." *The Journal of Thoracic and Cardiovascular Surgery*, vol. 67(6):883-4.

Japanese Article Eguchi (1987) "A Special Retracter for Stabilizing the Heart During Circumflex Coronary Grafting." *Kyobu Geka*, vol. 40(1):39-40.

Japanese Journal of Thoracic Surgery, vol. 42, No. 2, 1989.

Kazama, S. et al., "*Fabric Heart Retractor for Coronary Artery Bypass Operations*," The Annals of Thoracic Surgery, 55:1582-3, 1993.

Kolessov, M.D., "*Mammary Artery-Coronary Artery Anastomosis as Method of Treatment for Angina Pectoris*," Thoracic and Cardiovascular Surgery, vol. 54, No. 4, Oct. 1967, pp. 535-544.

Konishi, T. MD, et al., "*Hybrid-Type Stabilizer for Off-Pump Direct Coronary Artery Bypass Grafting*," Annals of Thoracic Surgery 66:961-2, 1998.

Kresh, et al., "*Heart-Mechanical Assist Device Interaction*," Trans. Am. Soc. Artif. Intern. Organs, vol. XXXII, 1986, pp. 437-443.

Lavergne, et al., "*Transcatheter Radiofrequency Ablation of a trial Tissue Using a Suction Catheter*," PACE, vol. 12, Jan. 1989, Part II, pp. 177-186.

Lonn, M.D., et al. "*Coronary Artery Operation Supported by the Hemopump: An Experimental Study on Pigs*," The Annals of Thoracic Surgery, vol. 58, No. 1, Jul. 1994, pp. 516-523.

Matsuura, A. MD, et al., "*A New Device for Exposing the Circumflex Coronary Artery*," The Annals of Thoracic Surgery, 59:1249-50, 1995, pp. 1249-1250.

McGee, et al. "*Extended Clinical Support with an Implatnable Left Ventricular Assist Device*," Trans. Am Soc. Artif. Intern. Organs, vol. XXXV, 1989, pp. 614-616.

McKeown, P.P. et al., "*A Modified Sternal Retractor for Exposure of the Internal Mammary Artery*," Ann. Thorac. Surg. 32 (1981) 619.

Ochsner, JL, et al., "*Surgical Management of Diseased Intracavitary Coronary Arteries*," The Annals of Thoracic Surgery, vol. 38, No. 4, July, pp. 356-362, Oct. 1984.

Parsonnet, V. MD, et al., "*Graduated probes for Coronary Bypass Surgery*," The Journal of Thoracic and Cardiovascular Surgery, vol. 68, No. 3, 424-26 (Sep. 1974).

Parsonnet, V. MD, et al., "*Self—Retaining Epicardial Retractor for Aortocoronary Bypass Surgery*," The Journal of Thoracic and Cardiovascular Surgery, 629-30 1979.

Perrault, L. et al., "*Snaring of the Target Vessel in Less Invasive Bypass Operations Does Not Cause Endothelial Dysfunction*," The Society of Thoracic Surgeons, pp. 751-755, 1997.

Pfister, et al., "*Coronary Artery Bypass Without Cardiopulmonary Bypass*," The Annals of Thoracic Surgery, vol. 54, No. 6, Dec. 1992, pp. 1085-1092.

Phillips, Steven J., M.D. et al., "*A Versatile Retractor for Use in Harvesting the Internal Mammary Artery and Performing Standard Cardiac Operations*," J. Thorac. Cardiovasc. Surg. (1989; 97:633-5).

Pilling Surgical Instruments, A Rusch International Company Brochure.

Pittman, John, M.D., et al., "*Improved Visualization of the Internal Mammary Artery with a New Retractor System*," Ann. Thorac. Surg., 1989; 48:869-70.

Riahi, et al., "*A Simple Technique and Device to Provide a Bloodless Operative Field in Coronary Artery Surgery Without Cross-Clamping the Aorta*," The Journal of Thoracic and Cardiovascular Surgery, vol. 66, No. 6., Dec. 1973, pp. 974-978.

Richenbacher, M.D., et al., "*Current Status of Cardiac Surgery: A 40-Year Review*," Journal of American College of Cardiology, vol. 14, No. 3, pp. 535-544.

Robicsek, F., "*Aortic Spoon-Jaw Clamp for Aorta-Saphenous Vein Anastomosis*," Journal of Cardiac Surgery, 10:583-585, 1995.

Robinson, et al., "*A Minimally Invasive Surgical Method for Coronary Revascularization—Preliminary Experience in Five Patients*," Circulation, Oct. 15, 1995, vol. 92, No. 8, 1-176.

Rousou, J. et al., "*Cardiac Retractor for Coronary Bypass Operations*," The Society of Thoracic Surgeons, pp. 52:877-52:878, 1991.

Roux, D. MD. et al., "*New Helper Instrument in Cardiac Surgery*," The Annals of Thoracic Surgery, 48: 595-6, 1989.

Roux, D., M.D. et al., "*Internal Mammary Artery Dissection: A Three Dimensional Sternal Retractor*," J. Cardiovasc. Surg., 1989; 30:996-7.

Ruzevich et al. "*Long-Term Follow-up of Survivors of Postcardiotomy Circulatory Support*," Trans. Am. Soc. Artif. Intern. Organs, vol. XXXIV, 1988, pp. 116-124.

Scholz, et al. "*Transfemoral Placement of the Left Ventricular Assist Device—Hemopump- During Mechanical Resuscitation*," Thoracic and Cardiovascular Surgeon, vol. 38 (1990) pp. 69-72.

Splittgerber et al.(1996) "Exposing the Circumflex Coronary Artery: The Heartflip Technique." *Ann Thorac Surg.*, vol. 61:1019-20.

Stevens, et al., "*Closed Chest Coronary Artery Bypass With Cardioplegic Arrest in the Dog*," $67^{th}$ Scientific Session, 238, I-251.

Trapp and R. Bisarya, "*To Use or Not to Use the Pump Oxygenator in Coronary Bypass Operations*," The Annals of Thoracic Surgery, vol. 19, No. 1, Jan. 1975, pp. 108-109.

Trapp, et al., "*Placement of Coronary Artery Bypass Graft without Pump Oxygenator*," Journal of the Society of Thoracic Surgeons and The Southern Thoracic Surgeons Assn. vol. 19, No. 1, Jan. 1975.

USSC Cardiovascular Thora-Lift J, United States Surgical Corporation, Norwalk, Connecticut, Product Brochure.

Vigano, M., "*Tecnica Operatoria*," Minerva Cardioangiologica, vol. 23-N. 6-7 (1975).

Vincent, J.G., "*A Compact Single Post Internal Mammary Artery Dissection Retractor*," Eur. J. Cardio-Thor. Surg. 3 (1989) 276-277.

Westaby, S. et al., "*Less Invasive Coronary Surgery: Consensus From the Oxford Meeting*," The Annals of Thoracic Surgery, 62:924-31, 1996.

Zumbro, et al., "*A Prospective Evaluation of the Pulsatile Assist Device*," The Annals of Thoracic Surgery, vol. 28, No. 2, Aug. 1979, pp. 269-273.

\* cited by examiner

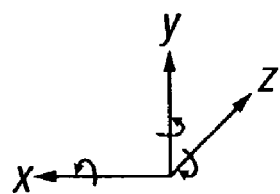
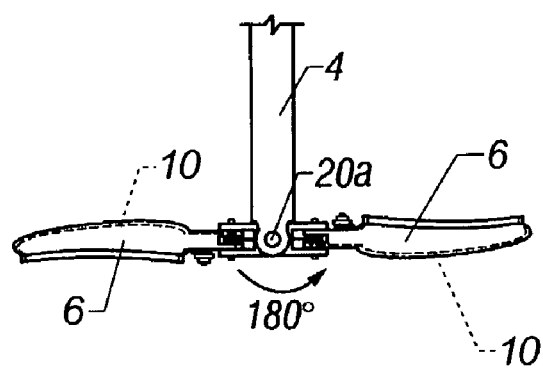
FIG. 1B
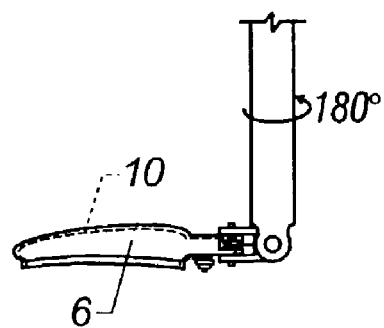
FIG. 1C

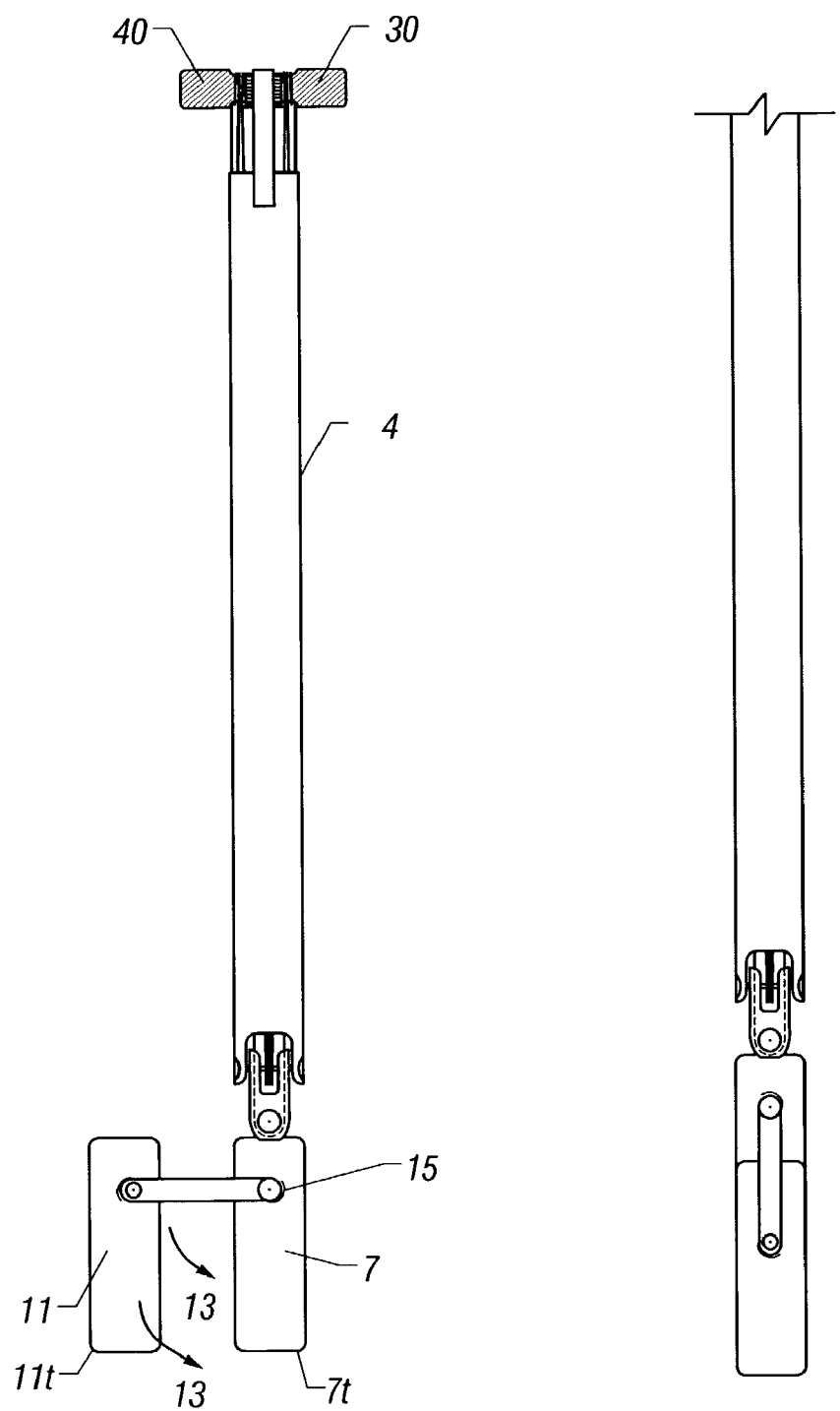
FIG. 2
FIG. 2A
FIG. 2B

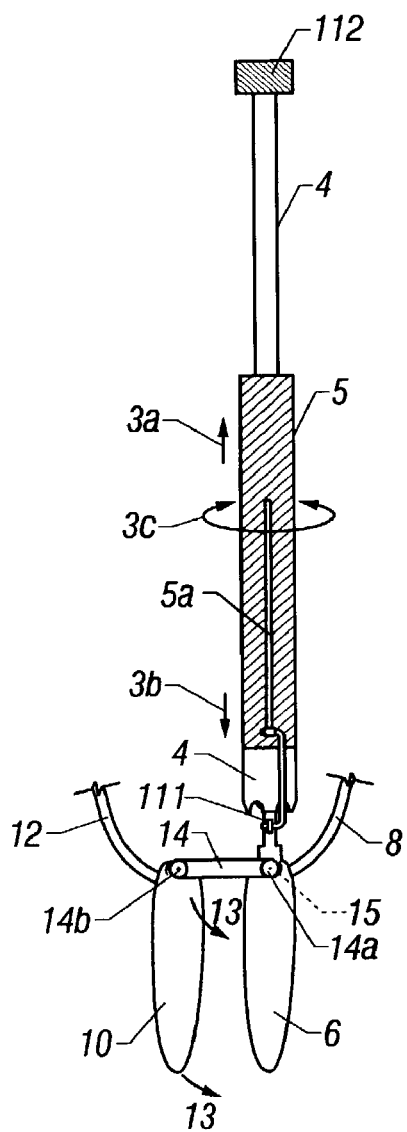
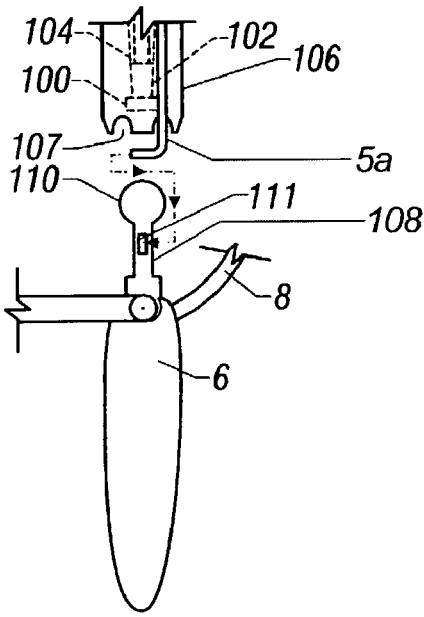
FIG. 4A
FIG. 4
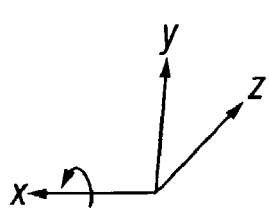
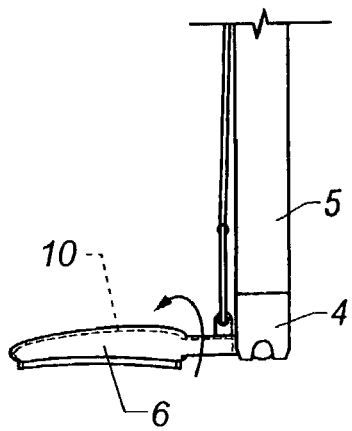
FIG. 4B

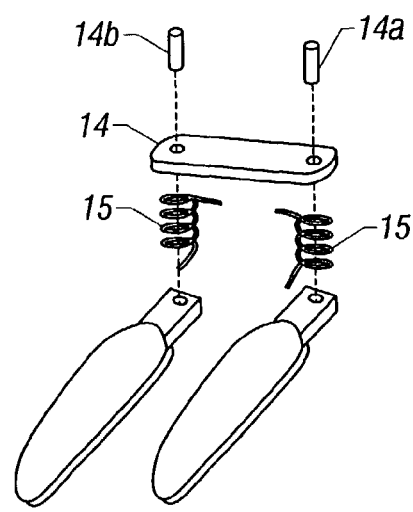
FIG. 7
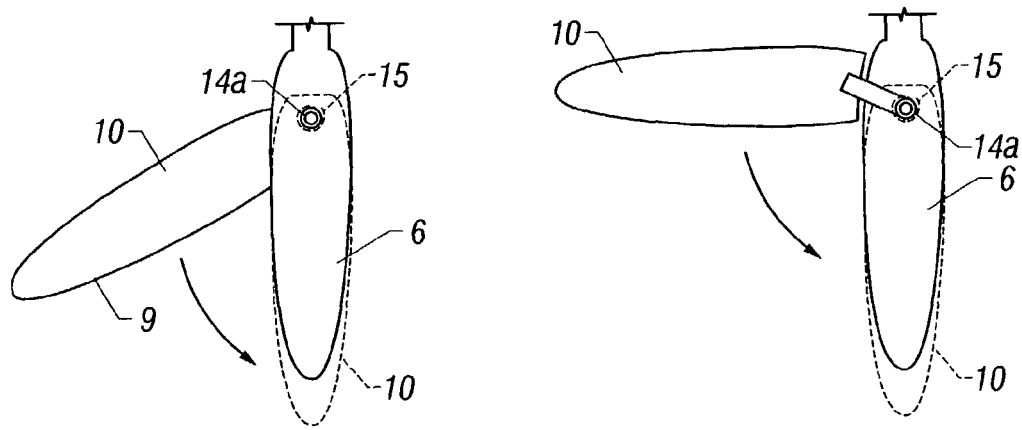
FIG. 8            FIG. 9

TISSUE STABILIZER AND METHODS OF USING THE SAME

FIELD OF THE INVENTION

The field of this invention is tissue stabilization, specifically stabilization of a beating heart.

BACKGROUND OF THE INVENTION

Certain surgical procedures require the surgeon to perform delicate surgical operations on tissues within the body that are moving or otherwise unstable. The ability to stabilize or immobilize a surgical site provides greatly improved surgical accuracy and precision and reduces the time required to complete a particular procedure. A large and growing number of surgeons are performing successful coronary artery bypass graft (CABG) surgery on the beating heart by temporarily stabilizing or immobilizing a localized area of the beating heart. Methods and apparatus for performing a CABG procedure on a beating heart are described in U.S. Pat. Nos. 5,894,843 and 5,727,569 to Benetti et al., the disclosures of which are herein incorporated by reference.

In a typical CABG procedure, a blocked or restricted section of coronary artery, which normally supplies blood to some portion of the heart, is bypassed using a source vessel or graft vessel to re-establish blood flow to the artery downstream of the blockage. This procedure requires the surgeon to create a fluid connection, or anastomosis, between the source or graft vessel and an arteriotomy or incision in the coronary artery. Forming an anastomosis between two vessels in this manner is a particularly delicate procedure requiring the precise placement of tiny sutures in the tissue surrounding the arteriotomy in the coronary artery and the source or graft vessel.

The rigors of creating a surgical anastomosis between a coronary artery and a source vessel or graft vessel demands that the target site for the anastomosis be substantially motionless. To this end, a number of devices have been developed which are directed to stabilizing a target site on the beating heart for the purpose of completing a cardiac surgical procedure, such as completing an anastomosis. Stabilization may be provided using a device that provides a mechanical or compression force to the tissue or by a device which applies a negative pressure to the tissue. Representative devices useful for stabilizing a beating heart are described, for example, in U.S. Pat. Nos. 5,894,843; 5,727,569; 5,836,311 and 5,865,730.

As beating heart procedures have evolved, regardless of whether compression or negative pressure has been used to stabilize or immobilize the heart, new challenges have arisen. For example, surgeons may gain access to the heart using a number of different approaches, both open and closed chest, such as through a sternotomy, mini-sternotomy, thoracotomy or mini-thoracotomy, or less invasively through a port provided within the chest cavity of the patient, e.g., between the ribs or in a subxyphoid area, with or without the visual assistance of a thoracoscope. Accordingly, the devices used to stabilize the heart must be configured to accommodate the particular approach chosen. For example, when a closed chest approach is used such as a port access approach wherein the device is introduced into the body cavity through a small access port or stab wound, the device must be designed to be advanced through such small openings without damaging the device or any internal body structures.

As such, there is continued interest in the development of new devices and methods for use for easily and effectively stabilizing or immobilizing tissue, e.g., a beating heart. Of particular interest would be the development of such devices and methods of use which may be used in a variety of surgical approaches, including a sternotomy, mini-sternotomy, thoracotomy, mini-thoracotomy, or less invasively through a port provided within the chest cavity of the patient, e.g., between the ribs or in a subxyphoid area, with or without the visual assistance of a thoracoscope.

SUMMARY OF THE INVENTION

Devices and methods of use thereof are provided for stabilizing tissue, e.g., a beating heart, within a patient's body. In certain embodiments, the subject devices are characterized by having a shaft and at least two contacting members operatively associated with the shaft where the contacting members are capable of substantial coaxial alignment when in a low profile configuration, such as when retained within a sheath, and also capable of assuming an open orientation when in a working configuration, e.g., when not constrained within a sheath. In certain other embodiments, the devices are characterized by having a shaft and at least one tissue contacting member associated with the shaft using a ball and socket mechanism, wherein the at least one tissue contacting member may be caused to pitch and/or roll and/or yaw. The subject devices are suitable for use in a variety of surgical approaches including sternotomies, mini-sternotomies, thoracotomies or mini-thoracotomies, or through a port provided within the chest cavity of the patient, e.g., between the ribs or in a subxyphoid area, with or without the visual assistance of a thoracoscope and, as such, may be configured to be inserted into a patient's chest cavity through a sheath. The subject devices may be configured to apply negative pressure to the target tissue, a compression force or both negative pressure and a compression force to stabilize tissue. In the subject methods, a subject device is advanced to the target site and stabilizes the target tissue using either compression, negative pressure or both compression and negative pressure. The subject invention also includes kits for use in practicing the subject methods.

It is an aspect of the invention to provide a tissue stabilizer and methods of use that can be introduced into a body cavity through a wide variety of access means including a sternotomy, mini-sternotomy, thoracotomy or mini-thoracotomy, or less invasively through a port provided within the chest cavity of the patient, e.g., between the ribs or in a subxyphoid area, with or without the visual assistance of an thoracoscope.

It is yet another aspect of the invention to provide a tissue stabilizer and methods of use that can be introduced into a body cavity through a sheath such as a cannula.

It is yet another aspect of the invention to provide a tissue stabilizer and methods of use that can be used to stabilize a wide variety of tissue, including a heart, and more specifically a beating heart.

It is an advantage that the subject invention can assume a low profile configuration characterized by substantially axially aligned tissue contacting members.

It is another advantage that the subject invention can be retained inside a sheath, e.g., a cannula, and advanced to the target site through the sheath.

It is an advantage that the subject invention can easily assume a working configuration from an assumed low profile configuration, where the working configuration is characterized by having open or spaced-apart tissue contacting members, e.g., parallel or substantially parallel oriented tissue contacting members.

It is yet another advantage that the subject invention can be remotely manipulated from a location outside the patient's body.

It is yet another advantage that the tissue contacting members of the subject invention may be caused to pitch, that is to rotate about a horizontal axis perpendicular to the main shaft.

It is yet another advantage that the tissue contacting members of the subject invention may be caused to yaw, that is to rotate about a vertical axis perpendicular to the main shaft.

It is yet another advantage that the tissue contacting members of the subject invention may be caused to roll, that is to rotate about the axis of the main shaft of the device.

It is yet another advantage that the subject invention may be configured to use negative pressure and/or compression forces to stabilize the target tissue.

These and other aspects, advantages and features of the present invention will become apparent to those persons skilled in the art upon reading the details of the presently described invention.

BRIEF DESCRIPTION OF THE DRAWINGS

FIG. 1B is a side view of the device of FIG. 1 showing the tissue contacting members pitching. FIG. 1C is a side view of the device of FIG. 1 showing the tissue contacting members yawing.

FIG. 2 shows the device of FIG. 1 having tissue contacting members configured to apply a compression force in a working configuration according to the subject invention. FIG. 2A shows the device of FIG. 2 in a low profile configuration. FIG. 2B shows a side view of the tissue contacting members of FIG. 2.

FIG. 4 shows an exemplary embodiment of a subject device configured to apply at least negative pressure in a working configuration according to the subject invention and having concentric shafts which enable the tissue contacting members to pitch and roll. FIG. 4A shows the device of FIG. 4 in a low profile configuration. FIG. 4B is a side view of the device of FIG. 4 showing the tissue contacting members yawing.

FIG. 7 shows an exploded view of an exemplary embodiment of the subject tissue contacting members and spring mechanism.

FIG. 8 shows an exemplary embodiment of the subject tissue contacting members operatively associated with each other without the use of attachment arm.

FIG. 9 shows an exemplary embodiment of the subject tissue contacting members wherein an attachment arm therebetween is pivotable about one end and fixed or immobile at the other.

DETAILED DESCRIPTION OF THE INVENTION

Figure 1:
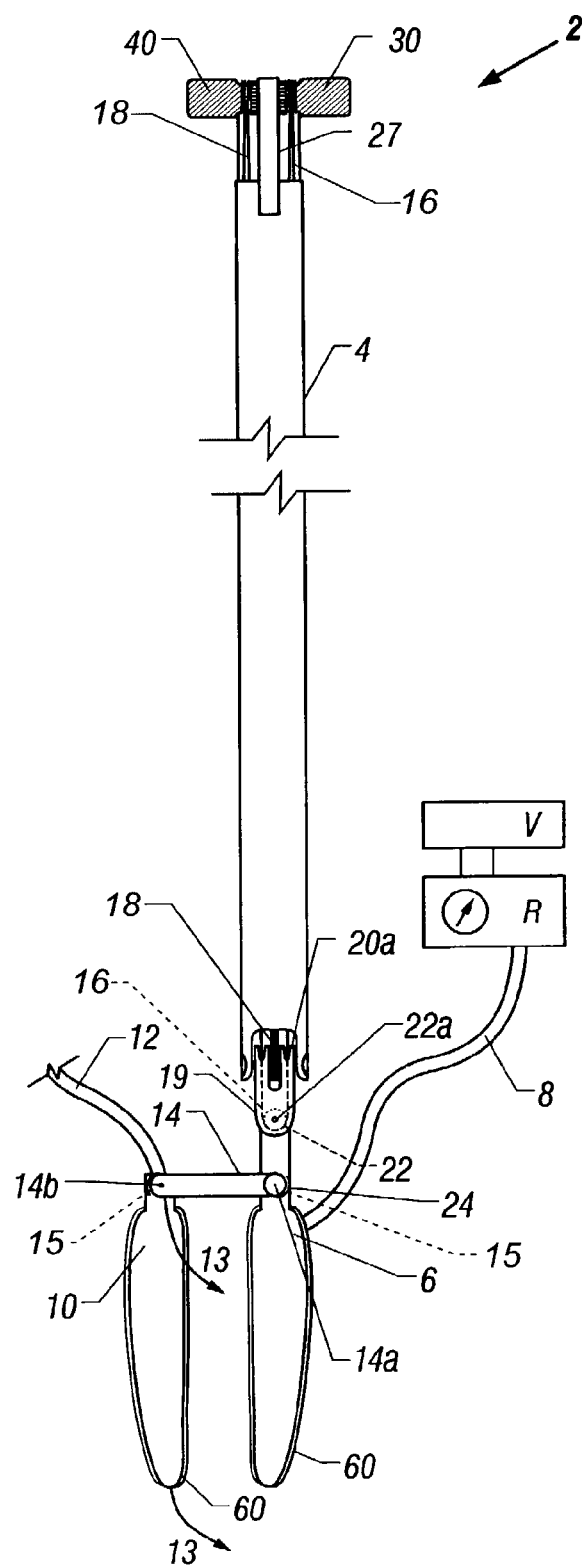
FIG. 1 is an exemplary embodiment of a tissue stabilizer configured to apply at least negative pressure in a working configuration according to the subject invention.

Devices and methods of use thereof are provided for stabilizing tissue, e.g., a beating heart, within a patient's body. In certain embodiments, the subject devices are characterized by having a shaft and at least two contacting members operatively associated with the shaft where the contacting members are capable of substantial coaxial alignment when in a low profile configuration, such as when retained within a sheath, and also capable of assuming an open orientation when in a working configuration. In certain other embodiments, the devices are characterized by having a shaft and at least one tissue contacting member associated with the shaft using a ball and socket mechanism, wherein the at least one tissue contacting member may be caused to pitch and/or roll and/or yaw. The subject devices are suitable for use in a variety of surgical approaches including sternotomies, mini-sternotomies, thoracotomies or mini-thoracotomies, or through a port provided within the chest cavity of the patient, e.g., between the ribs or in a subxyphoid area, with or without the visual assistance of a thoracoscope and, as such, may be configured to be inserted into a patient's chest cavity through a sheath. The subject devices may be configured to apply negative pressure to the target tissue, a compression force or both to stabilize the tissue. In the subject methods, a subject device is advanced to the target site and stabilizes the target tissue using either compression, negative pressure or both. The subject invention also includes kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a contacting member" includes a plurality of such contacting members and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject devices will be described first, followed by a detailed description of the subject methods. Following this section, subject kits which include the subject devices are reviewed.

Devices

As summarized above, generally the subject tissue stabilizing devices include a shaft to which at least two tissue contacting members are operatively associated. The subject devices may be used in a wide variety of surgical applications that require tissue to be stabilized or immobilized to provide a substantially stable and motionless surgical field on which a surgical procedure can be performed. By way of example only and not limitation, the subject devices described herein are directed to the stabilization of a portion of the heart to facilitate a surgical procedure on or within the heart, such as a coronary artery bypass graft (CABG) procedure to facilitate completion of an anastomosis, typically between a target coronary artery and a bypass graft or source vessel, without requiring cardiac arrest and cardiopulmonary bypass. However, it will be apparent to those of skill in the art that the subject invention may be used in a variety of surgical protocols where it is necessary to stabilize tissue.

The subject devices are configured to be used in a variety of surgical approaches including sternotomies, mini-sternotomies, thoracotomies or mini-thoracotomies, or through a port provided within the chest cavity of the patient, e.g., between the ribs or in a subxyphoid area, with or without the visual assistance of a thoracoscope and, as such, may be configured to be inserted into a patient's chest cavity through a sheath, e.g., a cannula. Accordingly, a feature of the subject devices is that they are capable of assuming a low profile configuration whereby the tissue contacting members are substantially axially aligned relative to one another to facilitate advancement to a target site, e.g., for advancement through and from a sheath, e.g., a cannula, in a low profile state. Once delivered to the target site, whether through a sheath or other suitable means, the subject devices are capable of assuming a working configuration, whereby the tissue contacting members have an open or spaced-apart orientation relative to one another so that a coronary artery may be positioned therebetween. As noted above, the subject devices may be configured to apply negative pressure to stabilize the target tissue and/or may be configured to apply a mechanical or compression force to the target tissue to provide stability. As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The subject devices will now be further described with respect to the Figures, where like numerals represent like features or components. FIGS. 1, 1A, 1B and 1C show an exemplary device according to the subject invention configured to employ at least negative pressure to stabilize tissue and FIGS. 2, 2A and 2B show device 2 of FIGS. 1, 1A, 1B and 1C configured to employ a compression force to stabilize tissue. That is, the tissue contacting members shown in FIGS. 1, 1A, 1B and 1C differ from the tissue contacting members shown in FIGS. 2, 2A and 2B in that the tissue contacting members of FIGS. 1, 1A, 1B and 1C are configured to employ at least negative pressure to stabilize tissue and the tissue contacting members of FIGS. 2, 2A and 2B are configured to employ a compression force to stabilize tissue. The subject devices will be described herein primarily with respect to device 2 and the components thereof of FIGS. 1, 1A, 1B and 1C, i.e., with reference to tissue contacting members 6 and 10, but it will be understood that such description is for exemplary purposes only and is in no way intended to limit the scope of the invention.

Accordingly, device 2 of FIG. 1 includes a shaft 4 and tissue contacting members 6 and 10 which engage tissue, e.g., the surface of the heart on opposite sides of a coronary artery. In this particular embodiment, two tissue contacting members 6 and 10 are shown, however any suitable number of tissue contacting members may be employed as appropriate, for example three or more tissue contacting members may be present.

Shaft 4 of device 2 is configured to position tissue contacting members 6 and 10 at the desired location on the heart and provide the necessary structure to hold the device substantially motionless against the forces generated by the heart. The size of shaft 4 may vary depending on the particular access approach used to access the heart, i.e., whether an open or closed chest procedure is employed. Generally, the length of shaft 4 will range from about 10 mm to about 100 mm or more, usually from about 15 mm to about 85 mm, usually from about 15 mm to about 75 mm, where the length of the shaft may be adjustable, e.g., telescopic. The diameter of the shaft will also vary, but typically will range from about 3 mm to about 20 mm, usually from about 3 mm to about 15 mm and more usually from about 5 mm to about 12 mm, where the shaft may have variable diameters. Such dimensions are exemplary only and are in no way intended to limit the scope of the invention.

Shaft 4 may also include at least one lumen therethrough, for example through which cable mechanisms or pushrods or other actuating elements and the like may be disposed, as will be further described below. In certain embodiments, shaft 4 of the present invention may further include additional lumens (not shown), e.g., for delivering ancillary instrumentation for facilitating the surgical procedure such as a thoracoscope, blower/mister, etc., for irrigation of the surgical site, and the like.

Shaft 4 may be fabricated from a variety of biocompatible materials having sufficient tensile strength to withstand a stabilizing force exerted on the heart. Suitable materials include, but are not limited to metals or alloys thereof and plastics, such as stainless steel, aluminum, titanium, Ultem, polycarbonate, glass-filled plastics, etc.

Shaft 4 may include one or more cables operatively associated with one or more tissue contacting members such that the tissue contacting members may be moved in a particular direction by remote manipulation of the one or more cables from a location outside the patient's body. Accordingly, as shown, device 2 includes at least two such cable mechanisms 16 and 18 which are actuated by turning respective actuators 30 and 40 positioned on the proximal end of the shaft 4, where actuator 30 and 40 may be any convenient actuator capable of actuating cables 30 and 40. (As used herein, the term "distal" refers to a portion of a device most proximal to the heart while the term "proximal" refers to the opposite portion which may extend outside of the patient's body and which is most often readily manipulated by the surgeon.) In this particular embodiment, at least a first cable, e.g., cable 16, may be correctly characterized as a yaw cable or yaw mechanism for directing the contacting members to yaw and at least a second cable, e.g., cable 18, may be correctly characterized as a pitch cable or pitch mechanism associated with pitch link 19 for directing the contacting members to pitch, as will be described in greater detail below. Additional cables may be employed (no shown), e.g., to move the contacting members close to or away from each other (i.e., move them between a low profile and a working configuration) from a location outside the patient's body.

Figure 3:
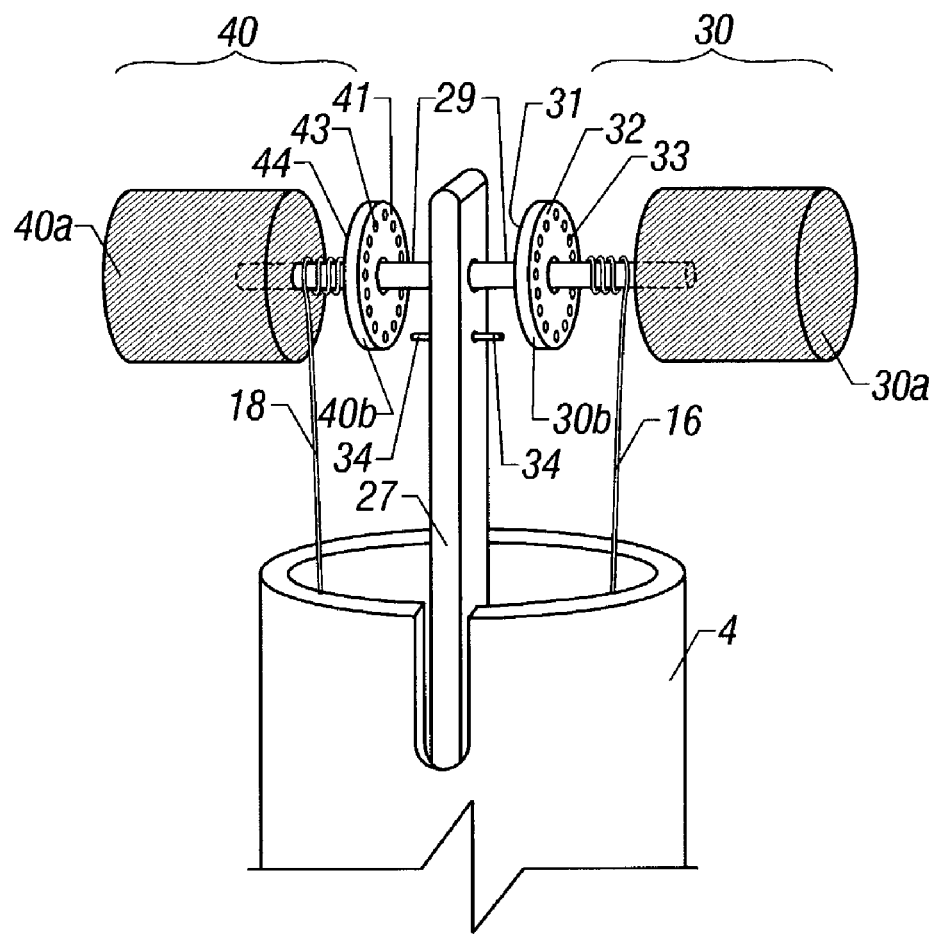
FIG. 3 shows an exemplary embodiment of an actuator according toe the subject invention.

The position of the tissue contacting members 6 and 10 may be locked to fix a particular position thereof and thus the subject devices may also include a locking mechanism, where any suitable locking mechanism may be used to fix the position of the tissue contacting members and will vary depending on the particular actuating mechanism used. FIG. 3 shows one such locking mechanism used to fix the positioning of the tissue contacting members 6 and 10. FIG. 3 shows an enlarged view of the proximal end of shaft 4 of FIG. 1 with actuators 30 and 40 and respective cables 16 and 18. The actuators are associated with shaft 4 by projection 27, which may lie completely inside shaft 4, as shown in FIG. 1, or may protrude or extend from the proximal end thereof, as shown in FIG. 3, and may be a unitary piece of construction with respect to the shaft 4 or may be a separate component which may be affixed to the shaft 4 with any convenient means such as welds, screws, adhesives, etc. The subject locking mechanism will now be described with respect to actuator 30, but it will be understood that such a description also applies to actuator 40 as well.

Actuator 30 includes a user grip or user contact element, herein shown as knob or button 30*a*, and locking wheel 30*b* and is rotatably positioned on post 29 of projection 27. The grips of the device will typically be ergonomically configured for ease and comfort of use. Actuator 30 is also slideably associated with post 29 such that actuator 30 may move in a direction away from and towards projection 27 slideably along post 29. Cable 16 is positioned between knob 30*a* and locking wheel 30*b* and operatively about yaw pivot link 22 such that turning knob 30*a* turns locking wheel 30*b* and moves cable 16 disposed therebetween, which causes the tissue contacting members to move in a predictable direction, as will be further described below.

Figure 3A:
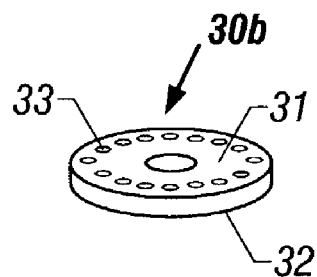
FIG. 3A shows a locking wheel of the device if FIG. 3.

FIG. 3A shows an enlarged view of locking wheel 30*b*. Locking wheel 30*b* has a first side 31, which faces projection 27, and a second side 32, which faces knob 30*a*. Positioned around the perimeter of at least first side 31 of locking wheel 30*b* is a plurality of recesses 33. The plurality of recesses 33 may be configured to extend the entire thickness of locking wheel 30*b*, i.e., extend completely through the locking wheel, to create through holes in locking wheel 30*b* or may extend only part of the way through locking wheel 30*b*, i.e., extend partially through the locking wheel. Regardless, the plurality of recesses 33 is configured to matingly engage pin 34 positioned on projection 27, where such engagement of wheel 30*a* and pin 34 prevents wheel 30*a* and thus actuator 30 from rotating, thereby fixing the relative position of cable 16 and preventing tissue contacting members 6 and 10 from moving. Disengagement of the locking wheel 30*b* from pin 34 allows rotation of knob 30*a* and locking wheel 30*b* about post 29 which moves cable 16 to, in turn, position tissue contacting members 6 and 10. In use, to move cables 16, actuator 30 is slideably moved in a direction away from projection 27 to disengage locking wheel 30*b* from pin 34. Knob 30*a* is turned to move cable 16, which in turn moves tissue contacting members 6 and 10. Once tissue contacting members 6 and 10 are positioned, their position may be fixed by slideably moving actuator 30 in a direction towards projection 27 such that pin 34 is inserted into a recess of locking wheel 30*b*.

Cable 18 functions in a manner analogous to that described for cable 16 such that respective actuator 40 includes a user grip or user contact element, herein shown as knob or button 40*a*, and locking wheel 40*b* and is rotatably positioned on post 29 of projection 27. Actuator 40 is also slideably associated with post 29 such that actuator 40 may move in a direction away from and towards projection 27 slideably along post 29. Cable 18 is positioned between knob 40*a* and locking wheel 40*b* and operatively about link 19 such that turning knob 40*a* moves cable 18 which in turn causes the tissue contacting members to move in a predictable direction.

As mentioned above, cables 16 and 18 are configured such that moving or actuating one of the cables, such as cable 18, causes the tissue contacting members 6 and 10 to pitch and moving the other cable, such as cable 16, causes the tissue contacting members 6 and 10 to yaw, where pitch, yaw and roll will be defined herein with respect to rotations about axes x, y and z. More particularly, pitch as used herein refers to rotation about the z-axis, yaw as used herein refers to rotation about the y-axis and roll as used herein refers to rotation about the x-axis.

FIG. 1B schematically shows a side view of a portion of device 2 of FIG. 1. As shown in FIG. 1B, tissue contacting members 6 and 10 are capable of pitching by rotating about a z-axis. To accomplish this pitch, tissue contacting members 6 and 10 pitch about pitch link 19 about 180°, as illustrated by the arrow. That is, actuating cable 18 rotatably moves pitch link 19 about pitch pin 20*a* about an axis perpendicular to its central axis which causes the tissue contacting members 6 and 10 to pitch.

Similarly, FIG. 1C again schematically shows a side view of a portion of device 2 of FIG. 1. As shown in FIG. 1C, actuating a second cable, such as cable 16, causes tissue contacting members 6 and 10 to yaw. To accomplish this yaw, tissue contacting members 6 and 10 yaw about yaw pivot link 22 about 180°, as illustrated by the arrow. That is, actuating cable 18 rotatably moves yaw pulley link 22 about yaw pin 22*a* about its central axis which causes the tissue contacting members 6 and 10 to yaw.

FIG. 4 shows an exemplary embodiment of another shaft configuration which enables remote actuation of the tissue contacting members 6 and 10 from a location outside a patient's body. Again, FIG. 4 is shown with reference to tissue contacting members 6 and 10, but it is to be understood that any such tissue contacting members may be used, such as tissue contacting members 7 and 11 shown in FIGS. 2-2B. In this particular embodiment, a second shaft 5 is positioned concentric with shaft 4, where second shaft 5 may be positioned within shaft 4 or, as shown here, about the exterior of shaft 4. Shaft 5 includes pitch pushrod or arm 5*a* which is associated at its distal end to tissue contacting member 6 utilizing pitch link 111 and associated to shaft 5 at its proximal end, where the arm 5*a* may be associated using any convenient means including physical, chemical and mechanical means such as welding, adhesives, etc. In certain embodiments, the pushrod is not integral with shaft 5. Moving shaft 5 proximally in the direction of arrow 3*a* or distally in the direction of arrow 3*b* correspondingly causes tissue contacting members 6 and 10 to pitch about an 180° axis. Turning the shaft 5 clockwise or counterclockwise in the directions of arrow 3*c* causes the tissue contacting members to roll. That is, turning the shaft 5 clockwise or counterclockwise in the directions of arrow 3*c* causes the tissue contacting members to rotate 360° about the x-axis, as shown in the side view of the device in FIG. 4C. Thus, the subject device is capable of assuming a variety of configurations which include all points or positions therebetween pitch and roll.

Figure 10:
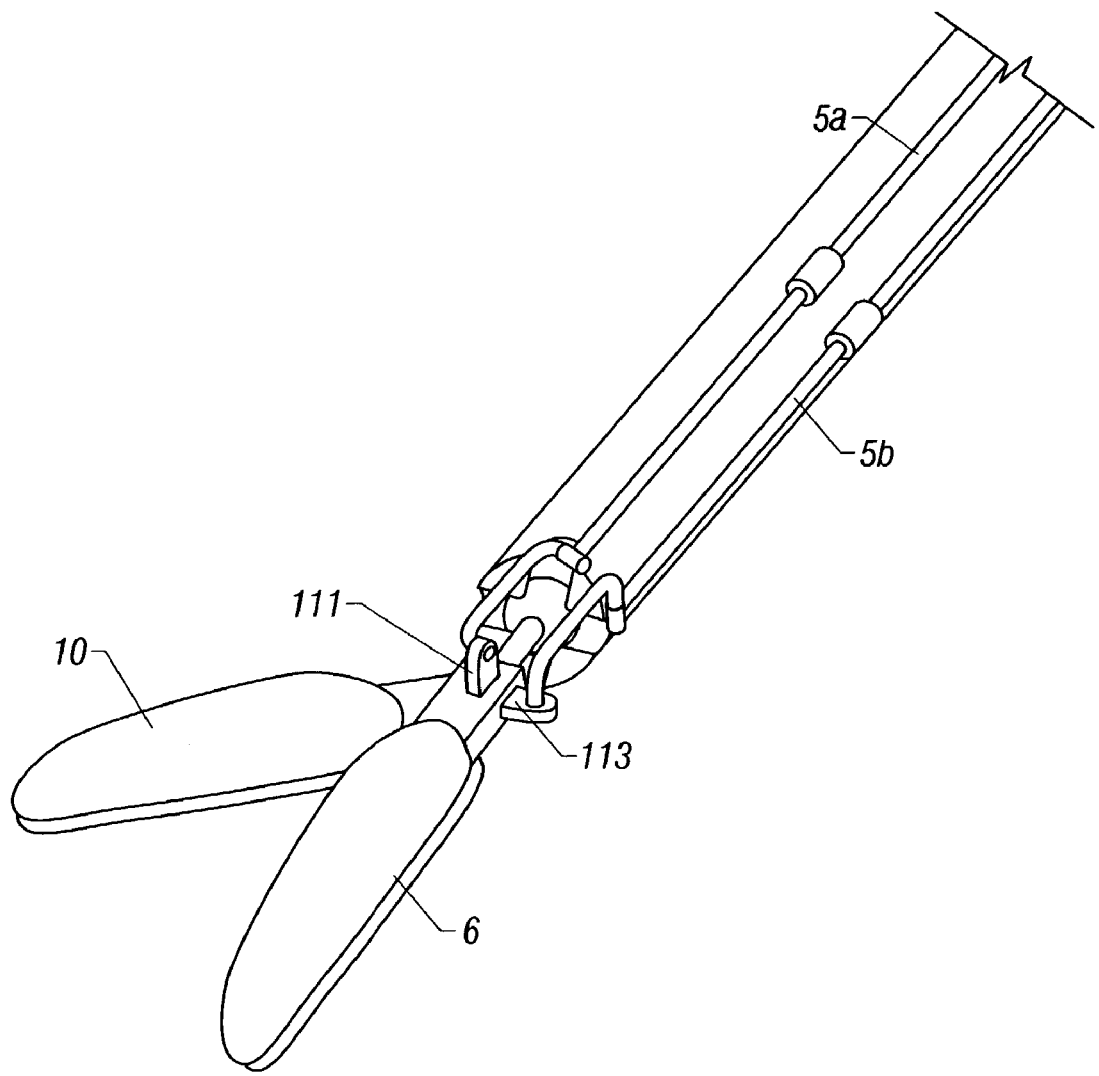
FIG. 10 shows an exemplary embodiment of the subject invention that is capable of pitching, rolling and yawing.

FIG. 10 shows a perspective view of another exemplary embodiment of the subject invention that is analogous to the device shown in FIG. 4 except that this particular embodiment includes a yaw pushrod or yaw arm 5*b* that enables the contacting members 6 and 10 to yaw. Yaw pushrod 5b is associated at its distal end to tissue contacting member 6 utilizing yaw link 113.

In all embodiments of the subject invention, the tissue contacting members may be attached to shaft 4 by the pivot links described above, or may employ a ball and socket mechanism, such as in FIGS. 4, 4A and 10. Accordingly, FIG. 4A shows an enlarged view of the ball and socket attachment means of FIG. 4, wherein the distal end of shaft 4, or alternatively of shaft 5, includes a socket 106 having a plurality of recesses 107 into which post 108 of a contacting member may be positioned. Ball 110 is receivable into socket 106 such that ball 110 moves freely when disposed within socket 106 and when post 108 is not positioned in a recess. Suitable ball and socket mechanisms are further described in co-pending, commonly assigned U.S. Ser. No. 09/118,132, the disclosure of which are herein incorporated by reference, as well as locking mechanisms which may also be used to lock the ball and socket mechanism described herein.

Referring again to the ball and socket configuration of FIGS. 4 and 4A, a locking ball joint is provided by including a block 100 within shaft 4 which conformingly contacts ball 110 to fix the position of ball 110. Such a locking ball joint is described in detail in U.S. application Ser. No. 09/975,392, filed Oct. 10, 2001 and titled "Surgical Instruments and Procedures for Stabilizing the Beating Heart During Coronary Artery Bypass Surgery", the disclosure of which is herein incorporated by reference. Block 100 is operatively associated with threaded push block 102, which in turn is operatively associated with a long telescoping keyed shaft and socket combination 104. Telescoping keyed shaft and socket combination 104 is actuated by thumbscrew 112 positioned at the upper end of shaft 4. In operation, a rotation of the thumbscrew 112 loosens the ball 110 to allow continuous positioning of contact members 6 and 10 relative to the shaft 4, while a counter-rotation locks the ball 110 into place by compressing block 100 against ball 110, fixing the position of tissue contacting members 6 and 10 relative to shaft 4.

As mentioned above, a feature of the subject invention is that the tissue contacting members are capable of assuming, in addition to the pitch, yaw and roll states described above, at least two delivery and deployment configurations wherein the contacting members are moveable relative to each other: a first low profile configuration that facilitates the delivery of a device to a target site, and a second working configuration. More specifically, the tissue contacting members of the device are capable of assuming substantial coaxial alignment with respect to each other, which substantial coaxial alignment provides a low profile configuration. The subject tissue contacting members are also capable of assuming a working configuration whereby the tissue contacting members are spaced-part from each other to provide a working space of suitable dimensions therebetween. Accordingly, the subject tissue contacting members are capable of easily moving between the above-described first low profile configuration and second working configuration, where a variety of mechanisms may be employed to accomplish this movement of the tissue contacting members, where exemplary embodiments will now be described.

In certain embodiments, a spring mechanism may be employed such that the tissue contacting members are operatively associated with each other by a spring mechanism that biases one or more contacting members into a particular configuration. As shown, for example, in FIGS. 1, 1A, 1B and 1C, tissue contacting member 10 is operatively associated with tissue contacting member 6 by spring loaded attachment arm 14, which includes spring elements 15. The spring element may be any suitable element capable of providing a spring force that enables the tissue contacting members to open or expand, i.e., spring open, from a low profile configuration to a working or spaced-apart configuration where suitable elements include, but are not limited to, torsion spring, flat-wire spring, and the like. FIG. 7 shows an exploded view of the tissue contacting members and spring mechanism.

Figure 1A:
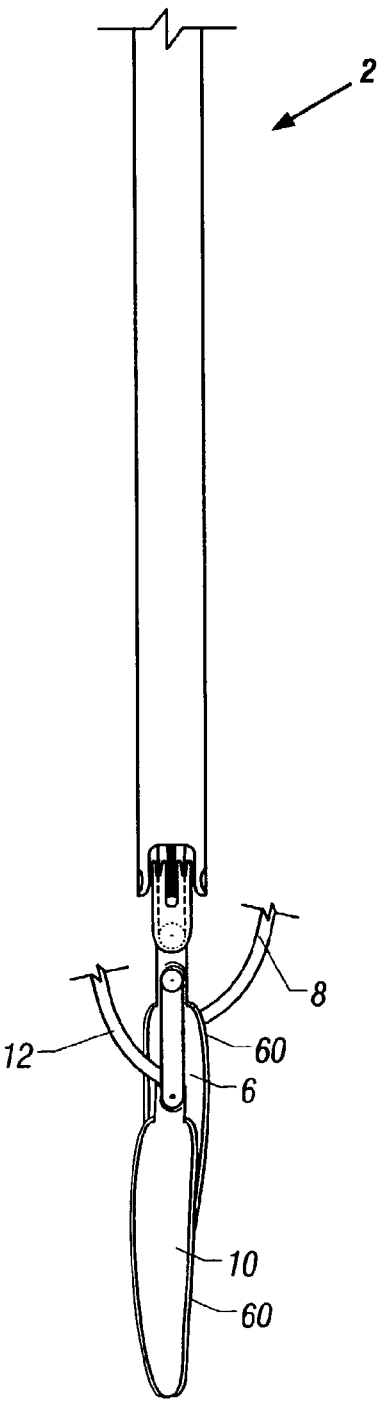
FIG. 1A shows the device of FIG. 1 in a low profile configuration.

Accordingly, spring element 15 of spring loaded attachment arm 14 biases tissue contacting members 6 and 10 in a working, open configuration where the tissue contacting members are spaced-apart, i.e., are not substantially coaxially aligned. FIGS. 1, 2 and 4 show the working configuration of the subject devices and FIGS. 1A, 2A and 4A show the low profile configurations thereof, respectively. More specifically, spring loaded attachment arm 14 biases tissue contacting member 10 in an open position relative to tissue contacting member 6 such that it is not axially aligned or overlapped with tissue contacting member 6 when in this biased, open configuration. Pins 14a and 14b of spring loaded attachment arm 14 enable tissue contacting member 10 to move in the direction of the arrow 13 (see FIG. 1) to assume a low profile configuration shown in FIG. 1A. That is, tissue contacting member 10 is rotatable about pin 14b where such a rotation enables tissue contacting member 10 to be substantially axially aligned with tissue contacting member 6 when moved in the direction of arrows 13 (see FIGS. 1A, 2A and 4A). Tissue contacting member 10 is capable of movement in the direction of arrow 13 by rotation of attachment arm 14 about pin 14a in the direction of arrows 13.

FIGS. 8 and 9 show alternative embodiments of operatively associating of tissue contacting members 6 and 10. FIG. 8 shows the contacting members attached without the use of attachment arm 14 such that tissue contacting member 10 is attached to tissue contacting member 6 at attachment point 9 that includes a single pin 14a and a spring element 15. Contacting member 10 is rotatable about pin 14a. Tissue contacting members 6 and 10 function in a manner analogous to that described above with regard to FIGS. 1, 1A, 1B, 1C, 2, 2A and 2B such that spring element 15 biases tissue contacting member 10 in an open position relative to tissue contacting member 6 such that it is not axially aligned or overlapped with tissue contacting member 6 when in this biased, open configuration and pin 14a enables tissue contacting member 10 to assume a low profile configuration (shown in phantom), such that it is substantially axially aligned with contact member 6. FIG. 9 shows another alternative embodiment analogous to that shown in FIGS. 1A, 1B, and 1C except that attachment arm 14 is pivotable about one end and fixed or immobile at the other. In other words, attachment arm 14 is fixed to contact member 10 such that it is immobile at the attachment point to contact member 10 and attached to contact member 6 at pin 14a such that it is moveable or rotatable about the pin. Analogous to that described above, spring element 15 biases tissue contacting member 10 in an open position relative to tissue contacting member 6 such that it is not axially aligned or overlapped with tissue contacting member 6 when in this biased, open configuration and pin 14a enables tissue contacting member 10 to assume a low profile configuration (shown in phantom), such that contact member 10 is substantially axially aligned with contact member 6.

In all embodiments, when the tissue contacting members are in a working configuration as shown for example in FIGS. 1, 2, 4 8 and 9, i.e., are not constrained such as by a sheath or other mechanical constraint, tissue contacting member 10 is biased in an open orientation, e.g., such that the tissue contacting member 10 is parallel or substantially parallel relative to tissue contacting member 6. That is, when in a working configuration, the tissue contacting members 6 and 10 are spaced-apart, typically substantially equidistantly, along their longitudinal lengths such that a coronary artery may be positioned therebetween. Typically, the tissue contacting members are configured so that the coronary vessel disposed therebetween, or at least the portion of the vessel of interest, is not contacted by the device, i.e., the tissue contacting members are spaced-apart a suitable distance so as not to adversely affect a vessel disposed therebetween. The positioning of attachment arm 14 above the plane of the target tissue, e.g., on an upper surface or non-tissue contacting side of the tissue contacting members 6 and 10 as shown for example in FIG. 1, enables tissue contacting members 6 and 10 to straddle a vessel therebetween without touching or otherwise adversely affecting the vessel.

In a low profile configuration (see for example FIGS. 1A, 2A and 4A), generally a first tissue contacting member, such as tissue contacting member 10, is caused to overlap, in whole or in part, a second tissue contacting member, such as tissue contacting member 6, such that the two contacting members are substantially coaxially aligned. More specifically, in a low profile configuration, tissue contacting member 10 is rotatable about pin 14b, if present, and spring loaded attachment arm 14 is rotatable about pin 14a such that the tissue contacting member 10 is capable of moving in the direction of the arrows shown to assume an axial alignment or substantial axial alignment with the tissue contacting member 6. That is, tissue contacting member 10 may be caused to move in a direction such that at least a portion of it overlaps a portion of the tissue contacting member 6. In certain embodiments, the width of the substantially coaxially aligned tissue contacting members in such a low profile configuration is no greater than the greatest width of any one tissue contacting member or at least the width is less than an inside diameter of a sheath, e.g., a cannula, into which it is to be placed. More specifically, the width will be no greater than about 3 mm to about 20 mm and usually no greater than about 5 mm to about 12 mm. However, the dimension of the width in the low profile configuration may change according to the width of the tissue contacting members employed.

As described above, tissue contacting member 10 may be caused to overlap at least a portion of tissue contacting member 6 such that the tissue contacting members 6 and 10 are substantially coaxially aligned. In certain embodiments, the tissue contacting member 10 may be moved into such a configuration by directly, manually moving the tissue contacting member 10 and, for example, retaining it in such a low profile configuration by constraining the tissue contacting members within a sheath. In other embodiments, the tissue contacting member may be moved by remote actuation of an actuator mechanism by the surgeon for selective actuation of the tissue contcting members 6 and 10 into low profile and working configurations. For example, the tissue contacting members may be associated with one or more cables (not shown) e.g., each tissue contacting member may be associated with a cable, instead of or in addition to the above-described spring mechanism, such that the one or more cables are configured to control the movement of one or more tissue contacting members between a first low profile configuration and a second working or spaced-apart configuration and all points therebetween. In this manner, from a position remote from the target site, a surgeon may selectively manipulate the relative positions of the contacting members with respect to low profile and working configurations using the one or more cables.

As mentioned above, the tissue contacting members may be configured to apply a compression force to the targeted tissue. In this case, the bottoms of the tissue contacting members may be designed to frictionally engage the surface of the heart, for example by using a textured surface or the like. Alternatively, or in addition to the above described compression force, negative pressure or vacuum may be applied to the tissue contacting members so that a portion of the beating heart contacted may be engaged or captured by the negative pressure created within a vacuum chamber or a plurality of negative pressure ports associated with the tissue contacting members. Accordingly, the subject tissue contacting members may assume a variety of configurations, where the particular shape and size of the tissue contacting members and will depend on a variety of factors such as the method of tissue stabilization, i.e., whether compression and/or negative pressure is used, the access approach used, i.e., whether a sternotomy, mini-sternotomy, thoracotomy, mini-thoracotomy, an access port provided within the chest cavity of the patient, e.g., between the ribs, or a subxyphoid approach is used, etc., Generally, the contact members may be substantially planar or may be slightly curved to conform to the shape of a heart and/or may be malleable.

As mentioned above, the tissue contacting members configured to apply negative pressure may assume a variety of shapes and sizes and may also include a thin, compliant seal 60 extending partially or completely around a perimeter of a bottom surface thereof, as shown in FIGS. 1 and 1A. For example, the shapes of the tissue contacting members may be oblong such as shown, for example, in FIGS. 1, 1A, 4 and 4A, or may assume a circular, polygonal, elliptical, rectangular, square, triangle shape, etc. or may assume a more complex or irregular shape, where the shapes of the contacting members may be the same or may be different. Likewise, the dimensions of the tissue contacting members may vary depending on a variety of factors including the design of the other features of the device or other instruments used to complete the anastomosis and the clinical assessment of the surgeon. By way of example only and not limitation, in those embodiments having a substantially oblong shape such as shown for example in FIGS. 1, 1A, 4 and 4A, the length may range from about 5 mm to about 100 mm and usually from about 5 mm to about 75 mm and the width typically ranges from about 5 mm to about 25 mm, usually from about 5 mm to about 20 mm and in certain embodiments the width may range from about 5 mm to about 8 or 10 mm, where the dimensions may vary as appropriate. The dimensions of the contacting members may be the same or may be different.

Each tissue contacting member configured to apply a negative pressure to the heart has a hollow interior defining a vacuum chamber. Example of suitable tissue contacting members that may be suitable for use with the present invention can be found, for example, in U.S. Pat. No. 6,036,641 and co pending U.S. application Ser. No. 09/305,811, filed May 4, 1999 and titled "Surgical Retractor Platform Blade Apparatus"; U.S. application Ser. No. 09/366,190, filed Aug. 3, 1999 and titled "Tissue Stabilizer and Methods of Use"; and U.S. application Ser. No. 09/769,964, filed Jan. 24, 2001 and titled "Surgical Instruments For Stabilizing a Localized Portion of a Beating Heart"; the disclosures of which are herein incorporated by reference.

In those embodiments employing negative pressure to stabilize the heart, the tissue contacting members will be coupled to a flow regulator R and vacuum source V, where such a regulator R and vacuum source V provide regulated negative pressure to the beating heart such that the pressure surrounding the tissue contacting members is reduced by opening negative pressure flow regulator R, thus enabling negative pressure to be applied to the beating heart. In the embodiment shown for example in FIG. 1, each tissue contacting member 6 and 10 is associated with a respective vacuum line 8 and 12, where each vacuum line is shown external to the shaft 4. However, in other embodiments, a single vacuum line may be used to provide a vacuum or negative pressure to all tissue contacting members. Furthermore, the one or more vacuum lines may be disposed within the shaft 4.

Likewise, in those embodiments employing a compression force to the heart, the size and shape of the tissue contacting members thereof may also vary. For example, the shapes of a tissue contacting member may be rectangular or such as shown in FIGS. 2, 2A and 2B, or may assume a circular, elliptical, polygonal, oblong, square, triangle shape, etc., or may assume a more complex or irregular shape, where the shapes of the contacting members may be the same or may be different. In certain embodiments, the tissue contacting members configured to apply a compression force may have frictional surfaces on the underside thereof to more securely engage the tissue that they contact, as mentioned above. Tips 7*t* and 11*t* of contact members 7 and 11, respectively, may be bent upwards in the forms of "ski tips" to prevent edge effects (e.g., stress concentration, cutting, chafing, etc.) against the tissue which might otherwise be caused by straight tips. FIG. 2B shows a side view of tissue contacting member 7 of FIG. 2 having a "ski tip" configured tip 7*t*′.

The dimensions of the compression applying tissue contacting members may vary depending on a variety of factors including the design of the other features of the device or other instruments used to complete the anastomosis and the clinical assessment of the surgeon. By way of example only and not limitation, in those embodiments having a substantially rectangular shape such as shown in FIGS. 2-2B, the length may range from about 5 mm to about 100 mm and usually from about 5 mm to about 50 mm and in certain embodiments the length may range from about 5 mm to about 25 or 30 mm. The width typically ranges from about 5 mm to about 25 mm, usually from about 5 mm to about 20 mm, where in certain embodiments the width may range from about 5 mm to about 8 or 10 mm, where the dimensions may vary as required. The dimensions of the contacting members may be the same or may be different.

Figure 5:
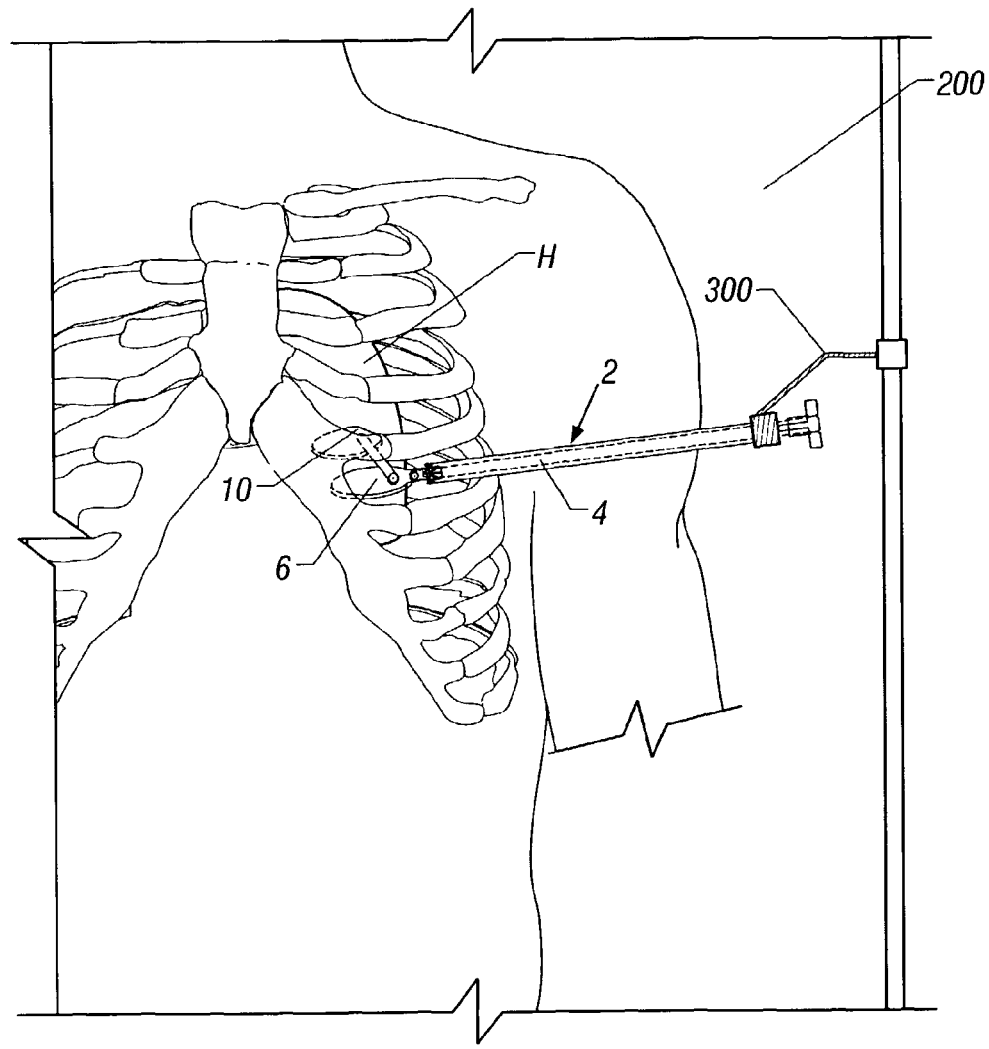
FIG. 5 shows a generic representation of the human thoracic cavity positioned on a table, wherein a subject device is positioned between the ribs and secured to the table by a securing device.

Regardless of the type of tissue contacting members employed with the subject device, the subject device may be maintained in a particular position by being secured to a stationary or fixed object such as a surgical table, surgical retractor, e.g., a sternal retractor, a portion of the patient's skeletal system, e.g., the sternum, the floor, the ceiling, and the like. As such, the subject device may itself be secured to a stationary or fixed object, i.e., the shaft of the subject device may be secured, e.g., with a mount, or the subject device may be associated with a means for attachment to a stationary or fixed object. For example, the subject invention may also include a securing member, where suitable securing members typically includes at least an arm, either flexible or rigid, a mount for attachment to a stationary object, as described above, and a means for associating the shaft of the subject device with the securing member. FIG. 5 shows a general representation of the human thoracic cavity positioned on a table 200. Device 2 is positioned between the fourth and fifth ribs such that tissue contacting members 6 and 10 are positioned on the heart H. Shaft 4 is secured to the table 200 using securing member 300 such that the position of the shaft is maintained in the respective position by securing member 300.

Figure 6:
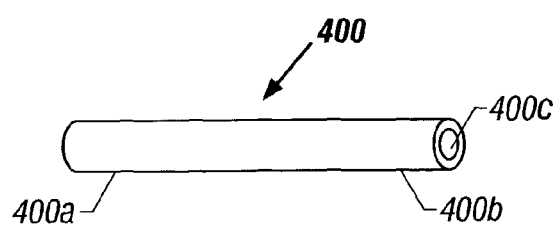
FIG. 6 shows a sheath suitable for use with the subject invention.

As described above, the subject devices may be retained in a delivery device such as a sheath, e.g., a cannula, where such a delivery device may also serve to constrain the tissue contacting members of the device in a low profile configuration. An exemplary embodiment of a delivery device suitable for use with the subject invention is shown in FIG. 6. Generally, the delivery device of the subject invention is a sheath 400 characterized by a proximal end 400*a*, a distal end 400*b* and at least one lumen 400*c* therebetween. The dimensions and material of such sheaths 400 depend on the type of approach or access route a surgeon employs to access the target tissue. A suitable sheath typically has at least one lumen with an internal diameter that is dimensioned to accommodate a subject device therein such that tissue contacting members are caused to assume and maintain a low profile configuration inside the sheath. Accordingly, the internal diameter of the sheath is dimensioned to be slightly greater than the width of the device when the device is in a low profile configuration. Typically, the internal diameter of the sheath ranges from about 5 mm to about 25-30 mm, more typically from about 5 to about 20-25 mm, and in certain embodiments ranges from about 5 mm to about 10 mm or from about 5 mm to about 12-15 mm, where such dimensions constrain a subject device therein in a low profile configuration. The length of a sheath 400 will typically range from about 4 inches to about 20 inches, usually from about 4 inches to about 12 inches and more usually from about 8 inches to about 12 inches. The sheaths of the subject invention may further include additional lumens for delivering ancillary instrumentation for facilitating the surgical procedure.

Methods

As summarized above, methods are also provided for stabilizing tissue within a patient's body. The subject methods may be used in a wide variety of surgical applications that require a tissue structure to be stabilized or immobilized to provide a substantially stable and motionless surgical field on which a surgical procedure can be performed. By way of example only and not limitation, the subject methods described herein are directed to the stabilization of a portion of the heart to facilitate a surgical procedure on or within the heart, such as a coronary artery bypass graft (CABG) procedure to facilitate completion of an anastomosis, typically between a target coronary artery and a bypass graft or source artery, without requiring cardiac arrest and cardiopulmonary bypass.

Generally, the subject methods involve accessing the beating heart by way of a sternotomy, mini-sternotomy, thoracotomy, mini-thoracotomy, port provided within the chest cavity of the patient, e.g., between the ribs, a subxyphoid access area, with or without the visual assistance of a thoracoscope, and advancing a subject device to the target site whereby the subject device is in a low profile configuration during advancement, i.e., the tissue contacting members of the subject device are substantially coaxially aligned. Once at the target site, the subject device is positioned around or adjacent a coronary artery to stabilize the tissue or rather the coronary artery. Once the target tissue is stabilized, the subject methods further include creating an arteriotomy in the stabilized coronary artery and anastomosing the bypass graft or source artery to the arteriotomy.

Thus, after the beating heart has been accessed, a subject device as described above is provided and advanced to the heart. More specifically, the subject device is advanced in a low profile configuration to the beating heart. That is, the subject device is advanced in a configuration such that at least a portion of the tissue contacting members overlap and the tissue contacting members are substantially coaxially aligned. In certain embodiments of the subject methods, e.g., when a closed-chest approach such as a port access approach or the like is employed, the subject device in a low profile configuration is advanced to the heart through a sheath, e.g., a cannula. However, the subject device may be advanced to the target site in a low profile configuration without the use of a sheath as well.

Regardless of whether a sheath is used or not, once the subject device has been brought to the site of the target tissue, it then assumes a working configuration wherein the tissue contacting members are spaced-apart relative to each other, as described above. That is, the tissue contacting members have a parallel or substantially parallel orientation relative to each other in this working state, such that a coronary artery may be positioned between the spaced-apart tissue contacting members. For example, in those embodiments employing a sheath to advance the subject device to the beating heart, once the subject device is advanced to a position outside the sheath, i.e., once the tissue contacting members are no longer constrained by the sheath, the tissue contacting members of the subject device will move or be urged such that they are no longer substantially axially aligned and are instead in a working configuration, i.e., are spaced-apart or are open relative to each other such as in a substantially parallel configuration with respect to each other. As described above, the tissue contacting members may be self-opening or expanding, i.e., may open automatically once no longer constrained, or may open with the aid of a surgeon, e.g., manually opened or opened using cables or the like from a position remote from the target site.

Once advanced out of the sheath and positioned in a working configuration, the subject device is then positioned about or adjacent a coronary artery to stabilize the tissue, or rather to stabilize the coronary artery positioned between the tissue contacting members. Typically, the tissue contacting members are positioned such that the coronary artery runs lengthwise in the space between the tissue contacting members.

As described above, the tissue is stabilized by applying negative pressure, a compression force or both a compression force and negative pressure to engage the surface of the heart. In those embodiments employing negative pressure, the tissue contacting members are brought into engagement with the tissue to be stabilized and then a vacuum is turned on to apply a negative pressure force or negative pressure to the target tissue.

Before or after negative pressure and/or compression force is applied, the subject device may be affixed to a stationery or fixed object such as a surgical table, surgical retractor, e.g., a sternal retractor, a portion of the patient's skeletal system, e.g., the sternum, the floor, the ceiling, and the like, where such a fixation may be accomplished by affixing the shaft of the device to an object or by securing the shaft to a suitable securing member, as described above, where the securing member is then affixed to an object. Still further, the device may be held in place by the surgeon or the surgeon's assistant, i.e., the shaft of the device may be held directly to hold the device in a fixed position.

Once the target tissue is stabilized or immobilized, i.e., once the device provides a substantially stable and motionless surgical field, an arteriotomy is then made in the stabilized coronary artery and a bypass graft or source vessel is then anastomosed to the arteriotomy. Although the particular source vessel and target artery of the anastomosis are determined clinically and of course may vary, a common bypass procedure on the beating heart, particularly when a minimally invasive procedure is employed, e.g., thoracotomy, mini-thoracotomy, port access, etc., includes an anastomosis which forms a connection between the left internal mammary artery (LIMA) as the source artery and the left anterior descending (LAD) as the target artery. In using the LIMA as a source vessel, the surgeon dissects a portion of the LIMA by separating it from the internal chest cavity, where such dissection may be performed before or after the heart has been stabilized. Once dissection of the LIMA is achieved, the surgeon may attach the dissected LIMA to the target artery, e.g., to the LAD, which has been stabilized according to the methods described above.

Following the procedure, the device is then removed from the surface of the beating heart and ultimately removed from the patient's body. For example, once the anastomosis is completed, vacuum is terminated if used, to disengage the tissue contacting members from the beating heart. Depending on the technique used to introduce the device into the body, the device may be removed from the body by again assuming a low profile configuration, as described above. In certain embodiments of the subject methods where the device had been retained inside a sheath and introduced to the target site through the sheath, the device may again assume a low profile configuration, be loaded back inside the sheath and removed from the body through the sheath. For example, when pulled back against the distal edge of the sheath, the tissue contacting members will be caused to assume a low profile configuration and the device may then be pulled back further into the sheath. Alternatively, if remote movement of the tissue contacting members is employed, the surgeon may directly move the tissue contacting members to a low profile state, e.g., by manipulating cables or the like associated with the tissue contacting members. Once the device is removed from the patient's body, the access site, i.e., the sternotomy, thoracotomy, access port, or the like, is then closed using conventional methods and the patient is prepared for post-op, as is known in the art, e.g., one or more drainage tubes may be placed, etc.

Kits

Also provided are kits for stabilizing tissue within a patient's body, such as a beating heart. The subject kits include at least one subject device, and oftentimes a plurality of such devices, where the devices may be the same or different, e.g., may be the same or different sizes and/or shapes, may include different types of devices, e.g., negative pressure devices and compression devices, etc. The kits may further include one or more sheaths, e.g., one or more cannulas, for delivering the subject device(s) to a target site and may also include one or more securing members for attaching the subject device(s) to a stationary or fixed object. In certain embodiments of the subject kits, one or more regulators are included for regulating the flow of a vacuum source to an organ. Finally, the kits may further include instructions for stabilizing tissue within a patient's body, e.g., instruction for using the subject devices for stabilizing tissue within a patient's body. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides an easy and effective way to stabilizing tissue within a patient's body, e.g., a beating heart or portion thereof. The above described invention provides a number of advantages, including ease of use, the ability to easily assume both low profile and working configurations, remote manipulation of the tissue contacting members from a location outside the patient's body, movement in at least one of pitch, yaw and roll and a combination or intermediate points therebetween, the ability to be configured to use negative pressure and/or compression, the ability to be used with a variety of tissues and use with both open and closed chest procedures, i.e., may be delivered through a sheath in the low profile configuration. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for stabilizing tissue within a patient's body, said device comprising:
    a shaft having a shaft longitudinal axis;
    a first contacting member having a first longitudinal axis and extending in a direction along said first longitudinal axis;
    a second contacting member having a second longitudinal axis and extending in a direction along said second longitudinal axis;
    wherein said first and second contacting members are mechanically linked to said shaft and movable relative to said shaft via a joint;
    said contacting members being configured to assume:
        (a) a low profile configuration in which said first and second longitudinal axes are in first and second positions respectively, in axial alignment with said shaft and in substantial coaxial alignment when viewed along a plane; and
        (b) a working configuration in which said first and second longitudinal axes are spaced apart;
    wherein upon moving said contacting members from said low profile configuration to said working configuration;
    said contacting members are spaced apart; and
    one of said first and second contacting members remains, at least temporarily, in said first or second position assumed in said low profile configuration.

2. The device according to claim 1, wherein said tissue is a beating heart.

3. The device according to claim 1, wherein said device is configured to apply negative pressure to said tissue.

4. The device according to claim 1, wherein said device is configured to apply a compression force to said tissue.

5. The device according to claim 1, wherein said at least two contacting members are capable of being moved from a remote location outside a patient's body.

6. The device according to claim 5, wherein said movement causes said at least two contacting members to pitch.

7. The device according to claim 5, wherein said movement causes said at least two contacting members to yaw.

8. The device according to claim 5, wherein said movement causes said at least two contacting members to roll.

9. A system for stabilizing tissue within a patient's body, said assembly comprising:
    a device according to claim 1; and
    a sheath, wherein at least a shaft of said device is movably disposed with said sheath.

10. The system according to claim 9, further comprising a securing means for securing said device to a stationary object.

11. The system according to claim 9, further comprising at least one regulator for regulating the flow of vacuum to an organ.

12. The system according to claim 9, further comprising a vacuum source operatively coupled to said device.

13. A kit for stabilizing tissue within a patient's body, said kit comprising:
    at least one device according to claim 1; and
    instructions for using said device to stabilize tissue within a patient's body.

14. The kit according to claim 13, comprising a plurality of devices.

15. The kit according to claim 13, further comprising at least one sheath for delivering said at least one device into a patient's body.

16. The kit according to claim 13, further comprising at least one securing means for securing said device to a stationary object.

17. The kit according to claim 13, further comprising at least one regulator for regulating a flow of vacuum.

18. The device of claim 1, wherein, in said working configuration, said contacting members are spaced apart and do not overlap in the plane, and are parallel to one another upon moving from said low profile configuration to said working configuration.

19. The device of claim 1, further comprising a biasing member that biases said first and second contacting members toward said working configuration.

20. A method for stabilizing tissue within a patient's body, said method comprising:
    positioning a first contacting member having a first longitudinal axis and a second contacting member having a second longitudinal axis, respectively, in a low profile configuration wherein said first and second longitudinal axes are contained in a plane in which a longitudinal axis of a shaft is contained, said shaft being connected to said first and second contacting members;
    advancing said first and second contacting members to a site of the tissue to be stabilized;
    repositioning at least one of said first and second contacting members to a working configuration in which said first and second contacting members are spaced apart from one another upon moving in a plane of movement from said low profile configuration to said working configuration, wherein one of said first and second longitudinal axes, in said working configuration remains, at least temporarily, in said plane with said longitudinal axis of said shaft, while the longitudinal axis of the other of said first and second contacting members is no longer contained within the plane; and
    contacting the tissue with contact surfaces of said first and second contacting members.

21. The method according to claim 20, wherein said device is advanced to said site through a sheath.

22. The method according to claim 21, wherein said sheath is a cannula.

23. The method according to claim 20, wherein said device is removed from said site through a sheath.

24. The method according to claim 23, wherein said sheath is a cannula.

25. The method according to claim 20, further comprising applying negative pressure through said contacting members to facilitate stabilization of the tissue.

26. The method according to claim 20, further comprising applying a compression force to said tissue to accomplish said stabilization.

27. The method according to claim 20, further comprising actuating movement of said contacting members in said working configuration from a remote location outside the patient's body.

28. The method according to claim 27, wherein said movement comprises pitching said contacting members relative to a remainder of said device.

29. The method according to claim 27, wherein said movement comprises yawing said contacting members relative to a remainder of said device.

30. The method according to claim 27, wherein said movement causes said at least two contacting members to roll.

31. The method according to claim 20, wherein said contacting members are introduced into a body cavity of the patient's body through an opening in the patient's body said opening being selected from one of the group consisting of sternotomy, mini-sternotomy, thoracotomy, mini-thoracotomy and a port.

32. The method according to claim 20, further comprising securing said device to a stationary object.

33. The method according to claim 20, further comprising performing a coronary artery bypass procedure on said stabilized tissue.

34. The method of claim 20, wherein in said working configuration, said contacting members are spaced apart and do not overlap in the plane, and are parallel to one another upon moving from said low profile configuration to said working configuration.

35. A device for stabilizing tissue within a patient's body, said device comprising:
   a shaft having a shaft longitudinal axis; and
   a first contacting member having a first longitudinal axis and a second contacting member have a second longitudinal axis, said first and second contacting members operatively associated with said shaft, said first contacting member extending in a direction along said first longitudinal axis and said second contacting member extending in a direction along second longitudinal axis, said contacting members being configured to assume a low profile configuration in which said first and second longitudinal axes and said shaft longitudinal axis are each contained in a plane, and a working configuration in which said first and second longitudinal axes are spaced apart and said contacting members are spaced apart upon moving from said low profile configuration to said working configuration; and one of said first and second longitudinal axes remains, at least temporarily, in said plane upon moving from said low profile configuration to said working configuration, wherein said contacting members are spaced apart and do not overlap in the plane when in said working configuration, and are parallel to one another upon moving from said low profile configuration to said working configuration.

36. A method for stabilizing tissue within a patient's body, said method comprising:
   positioning a first contacting member having a first longitudinal axis and a second contacting member having a second longitudinal axis, respectively, in a low profile configuration wherein said first and second contacting members are in substantial coaxial alignment and have first and second longitudinal axes, respectively, that are contained in a plane with a longitudinal axis of a shaft when in said low profile configuration, said shaft being connected to said first and second contacting members;
   advancing said first and second contacting members to a site of the tissue to be stabilized;
   repositioning at least one of said first and second contacting members to a working configuration in which said first and second contacting members are spaced apart from one another upon moving from said low profile configuration to said working configuration, one of said first and second longitudinal axes, in said working configuration remains, at least temporarily, in said plane, and said contacting members are parallel to one another upon moving from said low profile configuration to said working configuration; and
   contacting the tissue with said first and second contacting members.

* * * * *

UNITED STATES PATENT AND TRADEMARK OFFICE
CERTIFICATE OF CORRECTION

PATENT NO.         : 7,931,590 B2
APPLICATION NO.    : 10/283784
DATED              : April 26, 2011
INVENTOR(S)        : Willis It is certified that error appears in the above-identified patent and that said Letters Patent is hereby corrected as shown below:

Column 3, line 36, please delete "toe" and insert --to--;
Column 6, line 67, please delete "no shown" and insert --not shown--;
Column 9, line 52, please delete "spaced-part" and insert --spaced apart--;
Column 9, line 55, please delete "above-described," and insert --above described--;
Column 13, line 25, please delete "7t'" and insert --7t.--; and
Column 13, line 61, please delete "heart H." and insert --heart.--.

Signed and Sealed this
Twenty-fifth Day of September, 2012

David J. Kappos
*Director of the United States Patent and Trademark Office*